US011331269B2

(12) United States Patent
Jin et al.

(10) Patent No.: US 11,331,269 B2
(45) Date of Patent: May 17, 2022

(54) METHODS AND COMPOSITIONS TARGETING LUNG MICROBIOTA AND ITS RESPONDING IMMUNE PATHWAYS FOR LUNG CANCER TREATMENT

(71) Applicants: Massachusetts Institute of Technology, Cambridge, MA (US); The Broad Institute, Inc., Cambridge, MA (US)

(72) Inventors: Chengcheng Jin, Cambridge, MA (US); Georgia Lagoudas, Cambridge, MA (US); Paul Blainey, Cambridge, MA (US); Tyler Jacks, Newton, MA (US)

(73) Assignees: Massachusetts Institute of Technology, Cambridge, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 16/449,100

(22) Filed: Jun. 21, 2019

(65) Prior Publication Data
US 2020/0078296 A1 Mar. 12, 2020

Related U.S. Application Data

(60) Provisional application No. 62/769,215, filed on Nov. 19, 2018, provisional application No. 62/727,955, filed on Sep. 6, 2018.

(51) Int. Cl.
| A61K 45/00 | (2006.01) |
| A61K 9/00 | (2006.01) |
| A61P 35/00 | (2006.01) |
| C07K 16/24 | (2006.01) |
| C07K 16/28 | (2006.01) |
| A61K 31/43 | (2006.01) |
| A61K 31/7036 | (2006.01) |
| A61K 31/4164 | (2006.01) |
| A61K 38/08 | (2019.01) |
| A61K 31/7052 | (2006.01) |
| A61K 31/7048 | (2006.01) |
| A61K 31/7056 | (2006.01) |
| A61K 45/06 | (2006.01) |

(52) U.S. Cl.
CPC ........ *A61K 9/0073* (2013.01); *A61K 31/4164* (2013.01); *A61K 31/43* (2013.01); *A61K 31/7036* (2013.01); *A61K 31/7048* (2013.01); *A61K 31/7052* (2013.01); *A61K 31/7056* (2013.01); *A61K 38/08* (2013.01); *A61K 45/06* (2013.01); *A61P 35/00* (2018.01); *C07K 16/244* (2013.01); *C07K 16/245* (2013.01); *C07K 16/2866* (2013.01); *C07K 2317/21* (2013.01); *C07K 2317/24* (2013.01)

(58) Field of Classification Search
CPC .................................................. A61K 9/0073
See application file for complete search history.

(56) References Cited

U.S. PATENT DOCUMENTS

| 3,610,795 | A | | 10/1971 | Antoine | |
| 5,795,871 | A | * | 8/1998 | Narita | ................. A61K 31/7048 514/29 |
| 6,156,294 | A | * | 12/2000 | Mautone | ............. A61K 9/0043 424/45 |
| 9,624,298 | B2 | | 4/2017 | Nastri | |
| 2011/0281754 | A1 | * | 11/2011 | Fischer | .................. C12Q 1/689 506/9 |
| 2018/0371093 | A1 | * | 12/2018 | Bilic | ................ A61K 39/39558 |

FOREIGN PATENT DOCUMENTS

WO  2016097769  6/2016

OTHER PUBLICATIONS

Balassoulis et al (American Journal of Clinical Oncology vol. 31, No. 4, pp. 384-389) (Year: 2008).*
Bibby et al (European Respiratory Society Annual Congress, Publication No. P2930, Abstract No. 1255) (Year: 2013).*
Popowicz et al (PLOS One doi.org/10.1371/journal.pone.0188833) (Year: 2017).*
Lee et al (Advanced Drug Delivery Reviews vol. 133, pp. 107-130) (Year: 2018).*
Nakai et al (Chemotherapy vol. 40, No. 8, pp. 1077-1084) (Year: 1992).*
Agata, et al., "Expression of the PD-1 antigen on the surface of stimulated mouse T and B lymphocytes" Int. Immunol., 8:765-72 (1996).
Akbay, et al., "Interleukin-17A Promotes Lung Tumor Progression through Neutrophil Attraction to Tumor Sites and Mediating Resistance to PD-1 Blockade" J. Thorac. Oncol., 12:1268-79 (2017).
Akinosoglou, et al., "Infectious complications in patients with lung cancer" Eur. Rev. Med. Pharmacol. Sci., 17:8-18 (2013).
Albert, et al., "Azithromycin for prevention of exacerbations of COPD" N. Engl. J. Med., 365:689-98 (2011).

(Continued)

*Primary Examiner* — Albert M Navarro
(74) *Attorney, Agent, or Firm* — Pabst Patent Group LLP

(57) ABSTRACT

It has been discovered that lung tumor growth is associated with a dysregulation of the local microbiota, including an increased total bacterial load and reduced bacterial diversity in the airway. In the lungs, commensal bacteria, which are otherwise non-pathogenic and colonize pulmonary tissue at a much lower density in healthy individuals, provoke chronic inflammation and exacerbation of lung cancer through tumor-infiltrating immune cells. Thus, targeting the lung microbiota and its responding immune pathways is useful in treating lung cancer. Disclosed are compositions and methods targeting the lung microbiota and its responding immune pathways in a subject by specific targeting of commensal bacteria in the subject. Typically, the methods involve administering an effective amount of one or more therapeutics such as an antibiotic that reduces the local bacterial load, blocks or depletes tumor-infiltrating immune cells, and/or locally inhibits one or more cytokines or chemokines.

28 Claims, 15 Drawing Sheets

(56) References Cited

OTHER PUBLICATIONS

Anderson, et al., "Cutting edge: intravascular staining redefines lung CD8 T cell responses" J. Immunol., 189(6):2702-6 (2012).
Anderson, et al., "Intravascular staining for discrimination of vascular and tissue leukocytes" Nat. Protoc., 9(1):209-22 (2014).
Barbie, et al., "Systematic RNA interference reveals that oncogenic KRAS-driven cancers require TBK1" Nature, 462:108-12 (2009).
Bassis, et al., "Analysis of the upper respiratory tract microbiotas as the source of the lung and gastric microbiotas in healthy individuals" MBio., 6(2):e00037 (2015).
Biton, et al., "Independent component analysis uncovers the landscape of the bladder tumor transcriptome and reveals insights into luminal and basal subtypes" Cell Rep., 9:1235-45 (2014).
Borghardt, et al. "nhaled Therapy in Respiratory Disease: The Complex Interplay of Pulmonary Kinetic Processes" Can. Respir. J., 2018:2732017 doi: 10.1155/2018/2732017 (2018).
Bullard, et al., "Evaluation of statistical methods for normalization and differential expression in mRNA-Seq experiments" BMC Bioinformatics, 11:94 (2010).
Caporaso, et al., "Global patterns of 16S rRNA diversity at a depth of millions of sequences per sample" PNAS, 108 Suppl 1:4516-22 (2011).
Chang, et al., "T helper 17 cells play a critical pathogenic role in lung cancer" PNAS, 111:5664-9 (2014).
Cheng and Hu, "Lung-resident γδ T cells and their roles in lung diseases", Immunology., 151:375-84 (2017).
Cheng, et al., "Microbiota modulate tumoral immune surveillance in lung through a γδT17 immune cell-dependent mechanism" Cancer Res., 74:4030-41(2014).
Chmiel, et al., "Antibiotic management of lung infections in cystic fibrosis. I. The microbiome, methicillin-resistant *Staphylococcus aureus*, gram-negative bacteria, and multiple infections" Ann. Am. Thorac. Soc., 11 (7):1120-9 (2014).
Coffelt, et al., "Neutrophils in cancer: neutral no more", Nat Rev Cancer, 16:431-46 (2016).
Dempke, et al., "Second- and third-generation drugs for immuno-oncology treatment—The more the better" Eur J Cancer, 74:55-72 (2017).
Dickson, et al., "The Microbiome and the Respiratory Tract" Annu. Rev. Physiol., 78:481-504 (2016).
Dupage, et al., "Conditional mouse lung cancer models using adenoviral or lentiviral delivery of Cre recombinase" Nat. Protoc., 4(7):1064-72 (2009).
Gabay, "Cytokine inhibitors in the treatment of rheumatoid arthritis" Expert Opin. Biol. Ther., 2(2):135-49 (2002).
Gollwitzer, et al., "Lung microbiota promotes tolerance to allergens in neonates via PD-L1" Nat. Med., 20:642-7 (2014).
Govindan, et al., "Genomic landscape of non-small cell lung cancer in smokers and never-smokers" Cell, 150(6):1121-34 (2012).
Hamady and Knight, "Microbial community profiling for human microbiome projects: Tools, techniques, and challenges" Genome Res., 19:1141-52 (2009).
Hanahan, et al., "Hallmarks of Cancer: The Next Generation" Cell., 144:646-74, (2011).
Herbst, et al., "The biology and management of non-small cell lung cancer" Nature, 553(7689):446-54 (2018).
Houghton, et al., "Neutrophil elastase-mediated degradation of IRS-1 accelerates lung tumor growth" Nat. Med., 16:219-23 (2010).
Johnson, et al., "Recent clinical advances in lung cancer management" J. Clin. Oncol., 32:973-82 (2014).
Kamphorst, et al., "Beyond adjuvants: immunomodulation strategies to enhance T cell immunity" Vaccine, 33(0 2):B21-B28 (2015).
Kostelny, et al., "Formation of a bispecific antibody by the use of leucine zippers" J. Immunol., 148:1547-53(1992).

Leng, et al., "EBSeq: an empirical Bayes hierarchical model for inference in RNA-seq experiments" Bioinformatics, 29:1035-1043 (2013).
Ley, et al., "Ecological and evolutionary forces shaping microbial diversity in the human intestine" Cell, 124(4):837-48 (2006).
Li and Dewey, "RSEM: accurate transcript quantification from RNA-Seq data with or without a reference genome" BMC Bioinformatics, 12:323 (2011).
Li, et al., "Foxa2 and Cdx2 cooperate with Nkx2-1 to inhibit lung adenocarcinoma metastasis" Genes Dev., 29:1850-62 (2015).
Lloyd and Marsland, "Lung Homeostasis: Influence of Age, Microbes, and the Immune System" Immunity, 46:549-61 (2017).
Marsland and Gollwitzer, "Host-microorganism interactions in lung diseases" Nat. Rev. Immunol., 14:827-35 (2014).
Miettinen, et al., "Blind Source Separation Based on Joint Diagonalization in R: The Packages JADE and BSSasymp" J. Stat Softw., 76:1-31 (2017).
Palm, et al., "Immunoglobulin A coating identifies colitogenic bacteria in inflammatory bowel disease" Cell., 158(5):1000-10 (2014).
Papotto, et al., "IL-17+ γδ T cells as kick-starters of inflammation" Nat. Immunol., 18:604-11 (2017).
Picelli, et al., "Full-length RNA-seq from single cells using Smart-seq2", Nat. Protoc., 9:171-81 (2014).
Preheim, et al., "Distribution-based clustering: using ecology to refine the operational taxonomic unit" Appl. Environ. Microbiol., 79(21):6593-603 (2013).
Qiao, et al., "A retrospective study of risk and prognostic factors in relation to lower respiratory tract infection in elderly lung cancer patients" Am. J. Cancer Res., 5:423-32 (2015).
Rider, et al., "Biologies for Targeting Inflammatory Cytokines, Clinical Uses, and Limitations" Int. J. Cell Biol., 2016:9259646 (2016).
Roark, et al., "Subset-specific, uniform activation among V gamma 6/V delta 1+ gamma delta T cells elicited by inflammation" J. Leukoc. Biol., 75(1):68-75 (2004).
Romero, et al., "Keap1 loss promotes Kras-driven lung cancer and results in dependence on glutaminolysis" Nat. Med., 23:1362-8 (2017).
Rutledge and Bouveresse, "Independent components analysis with the JADE algorithm" Trac-Trend. Anal. Chem., 50:22-32 (2013).
Segal and Blaser, "A brave new world: the lung microbiota in an era of change" Ann. Am. Thorac. Soc., 11 Suppl 1:S21-7 (2014).
Siebert, et al., "Cytokines as therapeutic targets in rheumatoid arthritis and other Inflammatory diseases" Pharmacol. Rev., 67(2):280-309 (2015).
Singer, et al., "A Distinct Gene Module for Dysfunction Uncoupled from Activation in Tumor-Infiltrating T Cells" Cell, 171:1221-3 (2017).
Sommer and Backhed, "The gut microbiota—masters of host development and physiology" Nat. Rev. Microbiol., 11(4):227-38 (2013).
Songsivilai and Lachmann, "Bispecific antibody: a tool for diagnosis and treatment of disease" Clin. Exp. Immunol., 79:315-21 (1990).
Subramanian, et al., "Gene set enrichment analysis: a knowledge-based approach for interpreting genome-wide expression profiles" PNAS, 102:15545-50 (2005).
Tammela, et al., "A Wnt-producing niche drives proliferative potential and progression in lung adenocarcinoma" Nature, 545:355-9 (2017).
Turnbaugh, et al., "A core gut microbiome in obese and lean twins" Nature, 457(7228):480-4 (2009).
Vantourout and Hayday, "Six-of-the-best: unique contributions of γδ T cells to immunology" Nat. Rev Immunol., 13:88-100 (2013).
Wang, et al., "Inhibitors of neutrophil recruitment identified using transgenic zebrafish to screen a natural product library" Dis. Model Mech., 7(1):163-9 (2014).

* cited by examiner

FIG. 4E
FIG. 4F
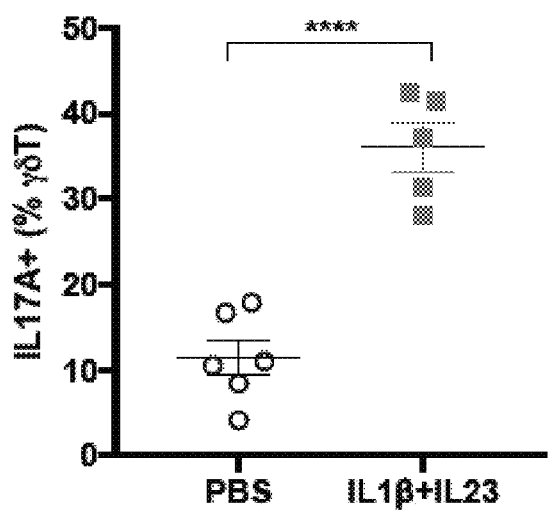
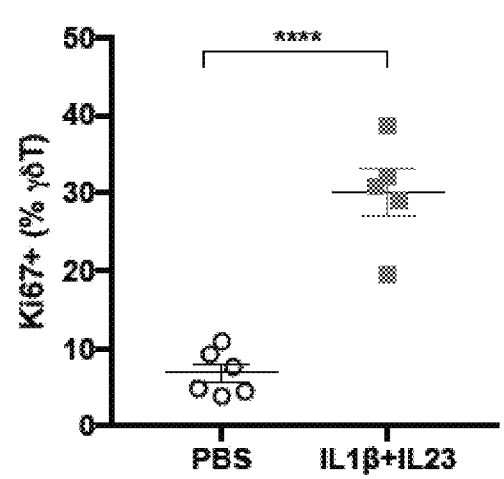
FIG. 5A
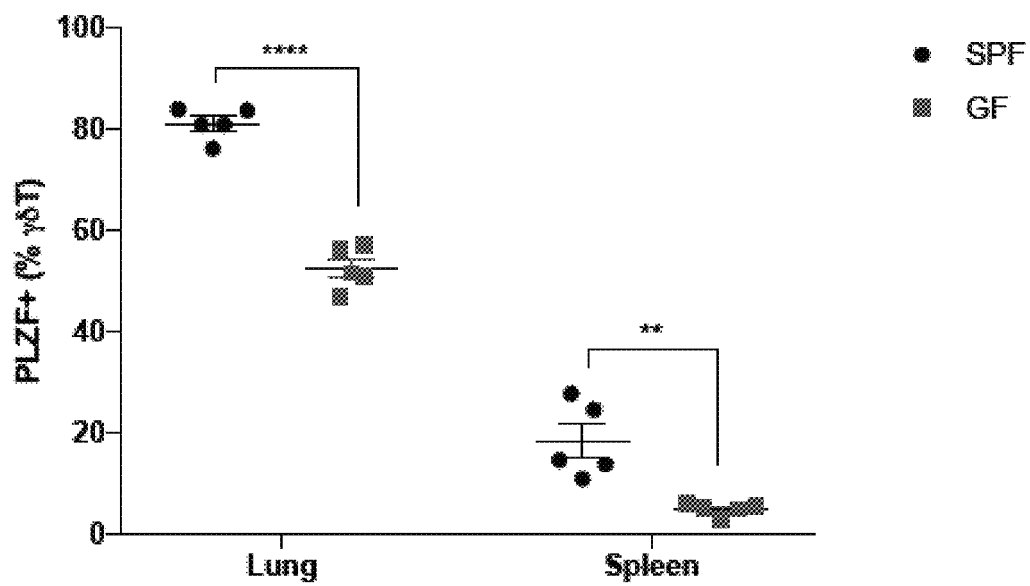

METHODS AND COMPOSITIONS TARGETING LUNG MICROBIOTA AND ITS RESPONDING IMMUNE PATHWAYS FOR LUNG CANCER TREATMENT

CROSS-REFERENCE TO RELATED APPLICATIONS

This application claims the benefit of and priority to U.S. Provisional Application No. 62/727,955 filed Sep. 6, 2018, and U.S. Provisional Application No. 62/769,215 filed Nov. 19, 2018, which are hereby incorporated by reference in their entirety.

STATEMENT REGARDING FEDERALLY SPONSORED RESEARCH OR DEVELOPMENT

This invention was made with Government Support under Grant No. CA185020 awarded by the National Institutes of Health (NIH), and Grant No. W81XWH-15-1-0623 awarded by the U.S. Army Medical Research and Material Command. The Government has certain rights in the invention.

FIELD OF THE INVENTION

The disclosed invention relates to the treatment of cancer and in particular, to the application of antibiotic and other therapeutic agents for the disruption of microbiota-induced inflammation and cancer cell proliferation in methods of lung cancer treatment.

BACKGROUND OF THE INVENTION

Lung cancer is the leading cause of cancer-related mortality worldwide in both men and women, with lung adenocarcinoma (LUAD) being the most common form of the disease (Herbst, et al., *Nature*, 553(7689):446-454 (2018)). Although the genomic landscape of LUAD has been extensively characterized (Govindan, et al., *Cell*, 150(6):1121-1134 (2012)), there is much less known about the tumor-cell extrinsic factors that control lung cancer development.

Mucosal surfaces exposed to the external environment are colonized by a vast number of microbes, collectively referred to as the commensal microbiota. There are approximately $10^{13}$-$10^{14}$ commensal bacteria colonizing the human body, primarily located in the gastrointestinal tract (Ley, et al., *Cell*, 124(4):837-848 (2006); Sommer and Backhed, *Nat. Rev. Microbiol.*, 11(4):227-238 (2013)). Healthy lungs were traditionally believed to be sterile; however, recent culture-independent 16S rRNA sequencing studies have identified the presence of microbial communities containing a complex diversity of bacteria in the lower respiratory tract (Dickson, et al., *Annu. Rev. Physiol.*, 78:481-504 (2016); Segal and Blaser, *Ann. Am. Thorac. Soc.*, 11 Suppl 1:S21-27 (2014)). This finding is consistent with the fact that, as a mucosal tissue harboring the largest surface area in the body, the lung is exposed to a variety of air-borne microbes and environmental insults through inhalation (Dickson, et al.).

In healthy individuals, the composition of the airway microbiota is diverse and well balanced. However, little is known about the microbiota in lung cancer patients. The course of lung cancer can be complicated by pulmonary infections in approximately 50-70% of cases (Akinosoglou, et al., *Eur. Rev. Med. Pharmacol. Sci.*, 17:8-18 (2013)). For example, post-obstructive pneumonia can negatively impact the efficacy of lung cancer therapy (Qiao, et al., *Am. J. Cancer Res.*, 5:423-432 (2015)). However, the role(s), if any, of local (airway) microbiota in development and progression of lung cancer is unknown and strategies for effective treatment are yet to be achieved. Furthermore, despite the recent development of targeted therapies for human LUAD, overall survival rates for this cancer remain very low (Herbst, et al.; Johnson et al., *J. Clin. Oncol.*, 32:973-982 (2014)).

Accordingly, there remains a need for improving the treatment of lung cancer to enhance overall survival rates of lung cancer patients.

Therefore, it is an object of the invention to provide compositions and methods for treating lung cancer.

It is another object of the invention to provide compositions and methods of targeting the lung microbiota and its responding immune pathways in subjects having lung cancer.

It is a further object of the invention to provide methods of treating lung cancer by reducing the local bacterial burden in the lungs, by blocking or depleting lung-resident immune cells, and/or by inhibition of cytokines and/or chemokines that promote tumor cell proliferation.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF SUMMARY OF THE INVENTION

Disclosed are compositions and methods of targeting the lung microbiota and its responding immune pathways in a subject having lung cancer. In some forms, the method comprises administering to the subject an effective amount of one or more therapeutics, where the administration of the therapeutics reduces the local bacterial load, blocks or depletes tumor-infiltrating immune cells, locally inhibits one or more cytokines or chemokines, or a combination thereof.

Also disclosed are compositions and methods of treating cancer (e.g., lung cancer) in a subject by specific targeting of commensal microbiota in the subject. An exemplary method involves treating lung cancer in a subject having lung cancer by administering to the subject an effective amount of one or more therapeutics that reduces cancer cell proliferation or viability and/or reduces tumor burden in the subject. The subject to be treated may not manifest standard clinical symptoms of infection (e.g., bacterial infection). In some forms, the treated subject has lung adenocarcinoma.

In some forms, administration of the therapeutics reduces the local bacterial load in the lungs. In some forms, the administration of the therapeutics blocks or depletes tumor-infiltrating immune cells in the lungs. In some forms, the administration of the therapeutics locally inhibits one or more cytokines and/or chemokines or locally inhibits cytokine and/or chemokine activity in the lungs. Exemplary cytokines and/or chemokines include IL-1β, IL-23, IL-17, IL-22, amphiregulin, CXCL2, PTGS2, IL-1R1, IL-23R, G-CSF, and IL-22R.

The method can further include analyzing the bacterial composition in a sample from the subject prior to the administration of the therapeutics. The analysis may include microbial culture and 16S-based sequencing steps. In some forms, the sample subjected to this analysis may be a sputum sample or bronchoscopy biopsy from the subject.

The subject that is treated may be identified as having an altered microbiota (e.g., bacterial population) compared to a healthy subject. For example, the subject may exhibit an increased total bacterial load and/or reduced bacterial diversity compared to a healthy subject. In some forms, the subject is identified as having one or more types of bacteria enriched in their lungs compared to a healthy subject. The enriched bacteria may include commensal bacteria from groups such as the Leuconostoceae, Sphingomonadaceae, Alphaproteobacteria, Herbaspirillum, Burkholderiales. In some forms, the therapeutic selectively targets, inhibits, or kills the enriched bacteria. Administration of the therapeutics may block or deplete tumor-infiltrating immune cells such as γδ T cells or neutrophils. In some forms, the γδ T cells or neutrophils may have been activated and/or stimulated to proliferate by lung microbiota (e.g., commensal bacteria) of the subject. In some forms, the γδ T cells may be positive for promyelocytic leukemia zinc finger (PLZF), CD27, CD44, CD69, and/or PD1.

The therapeutic administered in the method of treating cancer may include an antibiotic, antibody, small molecule, kinase inhibitor, siRNA, miRNA, aptamer, or natural or engineered autologous or allogenic immune cell. An antibiotic therapeutic may be a restricted spectrum antibiotic. Non-limiting examples of antibiotic therapeutics that may be used include ampicillin, neomycin, metronidazole, vancomycin, azithromycin, clarithromycin, clindamycin, or erythromycin. In some forms, the antibiotic therapeutic is in an inhalable and/or aerosolized form or formulation. In some forms, the antibiotic therapeutic is in an inhalable or aerosolized form or formulation. In some forms, the antibiotic therapeutic is in an inhalable and aerosolized form or formulation. In some forms, the therapeutic is an antibody such as, but not limited to, canakinumab (anti-IL1beta), secukinumab (anti-IL17), ixekizumab (anti-IL17), brodalumab (anti-IL17RA), risankizumab (anti-IL23), guselkumab (anti-IL23), or tildrakizumab (anti-IL23). The therapeutics used in accordance with the disclosed methods of treatment may be given by local administration.

In some forms, the therapeutic administered to the subject according to the provided methods is one or more other targeted therapies and/or immune-checkpoint blockage agents.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 2D) samples. Bacterial load in fecal pellets and BALF from untreated and antibiotic-treated SPF KP mice was measured by 16S rDNA-based qPCR; tumor burden was quantified at 15 weeks post tumor initiation. Data were normalized to the corresponding median value of each cohort, and the plots represent pooled data from 3 experimental cohorts.

FIGS. 4D-4F are graphs showing the number of total γδT cells (FIG. 4D) and the frequency of IL-17+(FIG. 4E) or Ki67+ (FIG. 4F) γδT cells at 36 hours post dosing with recombinant mouse IL-1β and IL-23.

FIGS. 5A-5E are graphs showing the expression of PLZF (FIG. 5A), CD27 (FIG. 5B), CD44 (FIG. 5C), CD69 (FIG. 5D), and PD1 (FIG. 5E) in γδ T cells from tumor-bearing lungs and spleens of SPF and GF mice. Results are expressed as the mean±SEM. *$p<0.05$,  $p<0.01$, * $p<0.001$, **** $p<0.0001$ by Student's t test. n=2-5 mice/group. Data represent 2-3 independent experiments.

FIG. 6E) in KP mice treated with the monoclonal antibody UC7-13D5 (which depletes γδ T cells).

DETAILED DESCRIPTION OF THE INVENTION

Figure 1A:
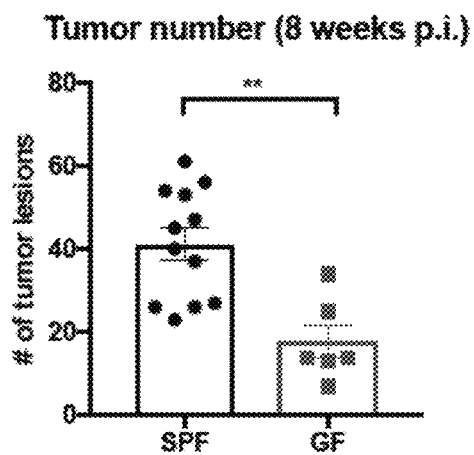
FIGS. 1A-1B are graphs showing tumor number in KP mice under germ-free (GF) and specific-pathogen-free (SPF) conditions at 8 weeks (FIG. 1A) and 15 weeks (FIG. 1B) post infection.
Figure 1B:
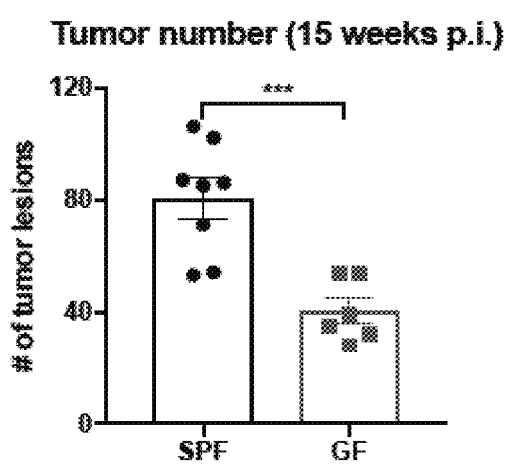
Figure 1C:
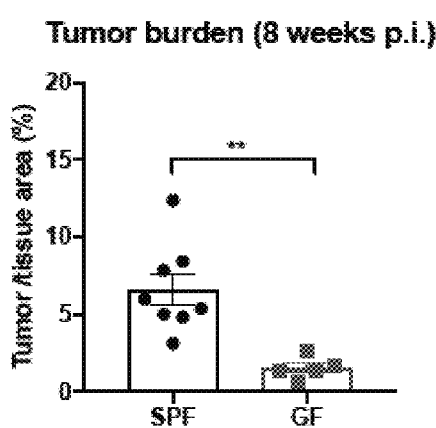
FIGS. 1C-1D are graphs showing tumor burden in KP mice under GF and SPF conditions at 8 weeks (FIG. 1C) and 15 weeks (FIG. 1D) post infection.
Figure 1D:
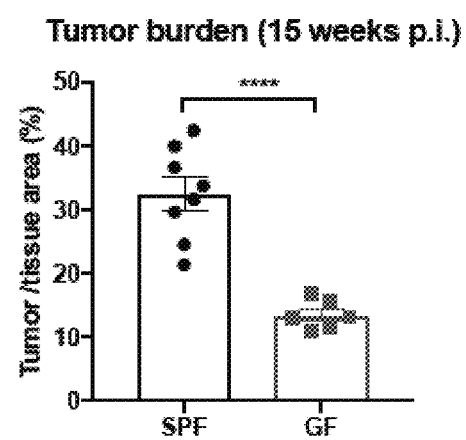

The disclosed method and compositions may be understood more readily by reference to the following detailed description of particular embodiments and the Examples included therein and to the Figures and their previous and following description.

Lung cancer is the leading cause of cancer-related mortality worldwide, with lung adenocarcinoma (LUAD) being the most common form of the disease (Herbst, et al.). Despite recent development of targeted therapies for some human LUAD subtypes, overall survival rates for this cancer remain very low. In approximately 50-70% of cases, the course of lung cancer is complicated by pulmonary infections (Akinosoglou, et al.). However, prior to the present disclosure, the specific contribution(s) of lung microbiota to development and progression of lung cancer was not known.

In the Examples described below, the host-microbiota interaction in lung cancer development was investigated using a genetically-engineered mouse (GEM) model driven by an activating point mutation of Kras and loss of p53, which are frequently associated with human lung adenocarcinoma (DuPage, et al., Nat. Protoc., 4(7):1064-72 (2009)). This autochthonous GEM model of LUAD not only faithfully mimics the genetic and histopathological features of the human disease, but also enables study of the complex crosstalk between the commensal microbiota and host immune system in the physiological context of developing lung cancer. Using this model, it has been discovered that lung tumor growth is associated with increased local bacterial burden and inflammation in the airway as compared to the healthy state. Depletion of microbiota through antibiotic treatment or re-deriving and maintaining mice in a germ-free (GF) status significantly reduced inflammation and suppressed the initiation and progression of lung cancer. Mechanistically, the local bacteria stimulated the proliferation and activation of lung-resident γδ T cells, which then produced a number of pro-inflammatory cytokines such as IL-17 that promoted neutrophil expansion and tumor cell proliferation. Blocking γδ T cells or their downstream effector molecules effectively inhibited lung tumor growth.

These results provide novel insights regarding the pathogenesis of lung cancer by revealing the role of commensal microbiota in shaping the tumor-associated immune response. Based on these results, cellular and molecular targets, as well as strategies for therapeutic intervention in lung cancer have been newly discovered. Such strategies include treating lung cancer by reducing the bacterial burden in the lung, by depletion or blocking of lung-resident immune cells, and by inhibition of cytokines and/or chemokines that promote tumor cell proliferation.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are methods of targeting the lung microbiota and its responding immune pathways in a subject having lung cancer. In some forms, the method comprises administering to the subject an effective amount of one or more therapeutics, where the administration of the therapeutics reduces the local bacterial load, blocks or depletes tumor-infiltrating immune cells, locally inhibits one or more cytokines or chemokines, or a combination thereof.

Also disclosed are methods of treating lung cancer in a subject having lung cancer. In some forms, the method comprises administering to the subject an effective amount of one or more therapeutics, where the administration of the therapeutics reduces cancer cell proliferation or viability and/or reduces tumor burden in the subject.

In some forms, the administration of the therapeutics reduces cancer cell proliferation or viability and/or reduces tumor burden in the subject. In some forms, the reduction in the local bacterial load, block or depletion of tumor-infiltrating immune cells, local inhibition of one or more cytokines or chemokines, or a combination thereof, reduces cancer cell proliferation or viability and/or reduces tumor burden in the subject.

In some forms, the reduction in the local bacterial load reduces cancer cell proliferation or viability and/or reduces tumor burden in the subject. In some forms, the block or depletion of tumor-infiltrating immune cells reduces cancer cell proliferation or viability and/or reduces tumor burden in the subject. In some forms, the local inhibition of one or more cytokines or chemokines reduces cancer cell proliferation or viability and/or reduces tumor burden in the subject. In some forms, the reduction in the local bacterial load and the block or depletion of tumor-infiltrating immune cells reduces cancer cell proliferation or viability and/or reduces tumor burden in the subject. In some forms, the reduction in the local bacterial load and the local inhibition of one or more cytokines or chemokines reduces cancer cell proliferation or viability and/or reduces tumor burden in the subject. In some forms, the block or depletion of tumor-infiltrating immune cells and the local inhibition of one or more cytokines or chemokines reduces cancer cell proliferation or viability and/or reduces tumor burden in the subject. In some forms, the reduction in the local bacterial load, the block or depletion of tumor-infiltrating immune cells, and the local inhibition of one or more cytokines or chemokines reduces cancer cell proliferation or viability and/or reduces tumor burden in the subject.

In some forms, the administration of the therapeutics reduces the local bacterial load in the lungs. In some forms, the administration of the therapeutics blocks or depletes tumor-infiltrating immune cells in the lungs. In some forms, the administration of the therapeutics locally inhibits one or more cytokines and/or chemokines or locally inhibits cytokine and/or chemokine activity in the lungs. In some forms, the administration of the therapeutics reduces the local bacterial load in the lungs and blocks or depletes tumor-infiltrating immune cells in the lungs. In some forms, the administration of the therapeutics reduces the local bacterial load in the lungs and locally inhibits one or more cytokines and/or chemokines or locally inhibits cytokine and/or chemokine activity in the lungs. In some forms, the administration of the therapeutics blocks or depletes tumor-infiltrating immune cells in the lungs and locally inhibits one or more cytokines and/or chemokines or locally inhibits cytokine and/or chemokine activity in the lungs. In some forms, the administration of the therapeutics reduces the local bacterial load in the lungs, blocks or depletes tumor-infiltrating immune cells in the lungs, and locally inhibits one or more cytokines and/or chemokines or locally inhibits cytokine and/or chemokine activity in the lungs.

In some forms, the subject does not manifest the standard clinical symptoms of infection. In some forms, the subject does not manifest the standard clinical symptoms of infection prior to the administration of the therapeutics.

In some forms, the method further comprises analyzing the bacterial composition in a sample from the subject. In some forms, the method further comprises, prior to the administration of the therapeutics, analyzing the bacterial composition in a sample from the subject. In some forms, the sample is a sputum sample or bronchoscopy biopsy. In some forms, the analysis comprises microbial culture and 16S-based sequencing.

In some forms, the subject is identified as having increased total bacterial load and/or reduced bacterial diversity compared to a healthy subject. In some forms, an increased total bacterial load and/or reduced bacterial diversity compared to a healthy subject is detected in the subject. In some forms, the subject is identified as having one or more types of bacteria enriched in the lungs of the subject compared to a healthy subject. In some forms, an enrichment of one or more types of bacteria is detected in the lungs of the subject compared to a healthy subject. In some forms, the one or more types of bacteria are commensal bacteria. In some forms, the commensal bacteria include bacteria from Leuconostoceae, Sphingomonadaceae, Alphaproteobacteria, Herbaspirillum, Burkholderiales.

In some forms, one or more of the therapeutics selectively targets, inhibits, kills, or a combination thereof, one or more of the types of the bacteria enriched in the lungs of the subject. In some forms, one or more of the therapeutics is selected for administration because it can selectively target, inhibit, kill, or a combination thereof, one or more of the types of the bacteria enriched in the lungs of the subject.

In some forms, the immune cells are γδ T cells, neutrophils, or a combination thereof. In some forms, the γδ T cells, neutrophils, or both were activated and/or proliferated by stimulation by lung microbiota of the subject. In some forms, the γδ T cells are positive for promyelocytic leukemia zinc finger (PLZF), CD27, CD44, CD69, and/or PD1. In some forms, the one or more cytokines and/or chemokines comprise one or more of IL-1β, IL-23, IL-17, IL-22, amphiregulin, CXCL2, PTGS2, IL-1R1, IL-23R, G-CSF, and IL-22R.

In some forms, the one or more therapeutics comprise one or more antibiotics, antibodies, small molecules, kinase inhibitors, siRNAs, miRNAs, aptamers, natural or engineered autologous or allogenic immune cells, or combinations thereof. In some forms, the one or more therapeutics comprises an antibiotic. In some forms, the antibiotic is a restricted spectrum antibiotic. In some forms, the antibiotic is in an inhalable or aerosolized form or formulation. In some forms, the antibiotic is ampicillin, neomycin, metronidazole, vancomycin, azithromycin, clarithromycin, clindamycin, or erythromycin.

In some forms, the one or more therapeutics comprises an antibody. In some forms, the antibody is canakinumab, secukinumab, ixekizumab, brodalumab, risankizumab, guselkumab, or tildrakizumab. In some forms, the lung cancer is lung adenocarcinoma. In some forms, the administration of the therapeutics is by local administration. In some forms, the one or more therapeutics further comprises one or more other targeted therapies and/or immune-checkpoint blockage agents.

In some forms, the administration of the therapeutics reduces cancer cell proliferation or viability and/or reduces tumor burden in the subject. In some forms, the reduction in the local bacterial load, block or depletion of tumor-infiltrating immune cells, local inhibition of one or more cytokines or chemokines, or a combination thereof, reduces cancer cell proliferation or viability and/or reduces tumor burden in the subject.

I. Definitions

As used herein, "enrich" or other forms of the word such as "enrichment" means to have an increased number, frequency, presence or proportion, to concentrate, or to be over-represented. It is understood that the term is typically in relation to some reference or expected value, i.e., it is relative, but that it is not always necessary for the standard or relative value to be referred to. The phrase "bacteria is enriched" may describe a particular population of bacteria that has an increased frequency among a mixed population of bacteria, or a particular population of bacteria that is over-represented in one condition (e.g., a diseased subject) as compared to another condition (e.g., a healthy subject). For example, a specific bacterial species that constitutes 60% of the total bacterial population in a sample from a lung cancer patient, but 2% in a corresponding sample from a healthy subject, may be described as enriched. In the context of nucleic acids or proteins, enrichment refers to an increase in the proportion of the nucleic acids or proteins in the sample relative to other molecules present or originally present in the sample. The measure of enrichment can be referred to in different ways. For example, enrichment can be stated as the percentage of all of the components that is made up by the enriched component. The term "enrich" may encompass, but does not necessarily denote any level of statistical significance.

"Tumor burden" or "tumor load" as used herein, refers to the number of cancer cells, the size or mass of a tumor, or the total amount of tumor/cancer in a particular region of a subject. Methods of determining tumor burden for different contexts are known in the art, and the appropriate method can be selected by the skilled person. For example, in some forms tumor burden may be assessed using guidelines provided in the Response Evaluation Criteria in Solid Tumors (RECIST).

"Bacterial load" means the quantity of bacteria in a subject, or region of a subject. In some forms, bacterial load may be expressed in colony forming units (CFU), bacterial genomic copies, or bacterial gene copies.

"Restricted spectrum" or "narrow spectrum" describes the characteristic of having limited activity against a population of targets (e.g., cells). For example, a restricted spectrum antimicrobial may be an antibiotic that is active against a selected group of bacterial types (e.g., Gram-negative bacteria, anaerobic bacteria, specific bacterial taxa, etc.).

"Tissue-resident," when used in the context of cells, describes the characteristic of being primarily, predominantly, or exclusively located in a specific region, organ or tissue. The region, organ or tissue may be healthy or diseased. The term specifically encompasses cells, such as immune cells, that may have previously migrated from a different region, organ or tissue (e.g., via the circulatory or lymphatic systems) and later infiltrate and/or persist locally in a specific (healthy or diseased) region, organ or tissue (e.g., a tumor). In a particular form, a tissue-resident cell that is resident in or infiltrates a tumorigenic region, organ or tissue, or a region, organ or tissue that later becomes tumorigenic, may be described as a "tumor-infiltrating" cell.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The term "inhibit" or other forms of the word such as "inhibiting" or "inhibition" means to decrease, hinder or restrain a particular characteristic such as an activity, response, condition, disease, or other biological parameter. It is understood that this is typically in relation to some standard or expected value, i.e., it is relative, but that it is not always necessary for the standard or relative value to be referred to. "Inhibits" can also mean to hinder or restrain the synthesis, expression or function of a protein relative to a standard or control. Inhibition can include, but is not limited to, the complete ablation of the activity, response, condition, or disease. "Inhibits" may also include, for example, a 10% reduction in the activity, response, condition, disease, or other biological parameter as compared to the native or control level. Thus, the reduction can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%, or any amount of reduction in between as compared to native or control levels. For example, "inhibits a cytokine/chemokine" means hindering, interfering with or restraining the expression and/or activity of the cytokine/chemokine or its downstream pathway relative to a standard or a control. In some forms, inhibition or reduction is relative to a state prior to administration of one or more therapeutics. In some forms, inhibition or reduction is relative to a control that is not administered one or more therapeutics.

"Treatment" or "treating" means to administer a composition to a subject or a system with an undesired condition (e.g., cancer). The condition can include one or more symptoms of a disease, pathological state, or disorder. Treatment includes medical management of a subject with the intent to cure, ameliorate, stabilize, or prevent a disease, pathological condition, or disorder. This includes active treatment, that is, treatment directed specifically toward the improvement of a disease, pathological state, or disorder, and also includes causal treatment, that is, treatment directed toward removal of the cause of the associated disease, pathological state, or disorder. In addition, this term includes palliative treatment, that is, treatment designed for the relief of symptoms rather than the curing of the disease, pathological state, or disorder; preventative treatment, that is, treatment directed to minimizing or partially or completely inhibiting the development of the associated disease, pathological state, or disorder; and supportive treatment, that is, treatment employed to supplement another specific therapy directed toward the improvement of the associated disease, pathological state, or disorder. It is understood that treatment, while intended to cure, ameliorate, stabilize, or prevent a disease, pathological condition, or disorder, need not actually result in the cure, amelioration, stabilization or prevention. In some specific forms, treatment means to administer a composition in an amount sufficient to reduce, alleviate or ameliorate one or more symptoms of a disorder, disease, or condition being treated. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

"Prevention" or "preventing" means to administer a composition to a subject or a system at risk for an undesired condition (e.g., cancer). The condition can include one or more symptoms of a disease, pathological state, or disorder. The condition can also be a predisposition to the disease, pathological state, or disorder. The effect of the administration of the composition to the subject can be the cessation of a particular symptom of a condition, a reduction or prevention of the symptoms of a condition, a reduction in the severity of the condition, the complete ablation of the condition, a stabilization or delay of the development or progression of a particular event or characteristic, or reduction of the chances that a particular event or characteristic will occur.

As used herein, the terms "effective amount" or "therapeutically effective amount" means a quantity sufficient to alleviate or ameliorate one or more symptoms of a disorder, disease, or condition being treated, or to otherwise provide a desired pharmacologic and/or physiologic effect. Such amelioration only requires a reduction or alteration, not necessarily elimination. The precise quantity will vary according to a variety of factors such as subject-dependent variables (e.g., age, immune system health, weight, etc.), the disease or disorder being treated, as well as the route of administration, and the pharmacokinetics and pharmacodynamics of the agent being administered.

As used herein, the terms "antibody" or "immunoglobulin" are used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv. Fragments are produced by recombinant DNA techniques, or by enzymatic or chemical separation of intact immunoglobulins. The term "antibody" also includes one or more immunoglobulin chains that are chemically conjugated to, or expressed as, fusion proteins with other proteins. The term "antibody" also includes a bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.*, 79:315-321 (1990); Kostelny, et al., *J. Immunol.*, 148, 1547-1553 (1992).

The term "small molecule," as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

II. Compositions

Compositions for use in the disclosed methods are disclosed. For example, compositions for use in methods of targeting the lung microbiota and its responding immune pathways in a subject in need thereof are disclosed. As another example, compositions for use in methods of treating cancer (e.g., lung cancer) in a subject in need thereof are disclosed. Also disclosed are compositions for use in methods of reducing or ameliorating one or more symptoms of cancer (e.g., lung cancer) in a subject in need thereof. Also disclosed are compositions for use in methods of reducing cancer cell proliferation or viability and/or reducing tumor burden in a subject in need thereof. The purpose and use of the disclosed compositions is, for example, as a therapeutic in a disclosed methods of targeting the lung microbiota and its responding immune pathways and of cancer treatment. In some forms, the therapeutics can reduce the local bacterial load, block or deplete tumor-infiltrating immune cells, locally inhibit one or more cytokines or chemokines, or a combination thereof. Such therapeutics can include antimicrobials, anti-inflammatories, anti-cancer, or more specific drugs for targeting the lung microbiota and/or its responding immune pathways or for inhibition of the cancer (e.g., lung cancer) to be treated. The therapeutic could encompass any compound or entity, such as a small organic molecule, peptide or nucleic acid, which would, regardless of mechanism, be suitable for use to treat cancer. The disclosed compositions can include small molecules, therapeutic polypeptides, antibodies, aptamers, inhibitory nucleic acids (e.g., miRNAs, piRNAs and siRNAs) or combinations thereof. In some forms, the therapeutic is an antimicrobial, such as for example, an antibiotic.

A. Inhibitors of Microbiota

Recent techniques of microbial identification have revealed that the lungs, previously considered sterile in health, harbor diverse communities of microbes. The terms "microbiome" or "microbiota" refer to the community of microscopic cells (e.g., bacteria, fungi), viruses, and phages that occupy a site (e.g., an organ or tissue). This encompasses the ecological community of commensal, symbiotic, and pathogenic microorganisms that share the site. Though relatively little is known about the contribution of viruses, phages, and fungi to the lung microbiome, bacterial components of the lung microbiome are being identified. However, prior to this disclosure, it was unclear how the commensal microbiota interact with developing tumor cells during malignant transformation, and specifically how the local bacterial component of the microbiota regulates the balance between tumor-promoting inflammation and anti-tumor immunity at distinct mucosal sites.

As demonstrated in the Examples, it has been discovered that lung tumor growth is associated with a dysregulation of the local microbiota, including an increased total bacterial load and reduced bacterial diversity in the airway. This suggests that tumor-associated barrier defects and airway obstruction might result in impaired bacterial clearance and altered growth conditions for microbes.

As such, disclosed are antimicrobials to be used as therapeutics in methods of treating lung cancer in a subject having lung cancer. In some forms, the therapeutics reduce cancer cell proliferation or viability and/or reduce tumor burden in the subject by reducing the local microbiota load (e.g., bacterial, viral or fungal load) in the affected area of the subject (e.g., the lung of a subject having lung cancer). Antimicrobials generally refer to agents that can be used to stop and/or kill microorganisms (e.g., bacteria, fungi, protozoa, and viruses) and as such, includes but is not limited to, antibiotics, antifungals, antiprotozoals, and antivirals.

i. Antibiotics

Preferably, the antimicrobial therapeutic is an antibiotic. In some forms, the therapeutic (e.g., antibiotic) selectively targets, inhibits, kills or a combination thereof, one or more of the types of the bacteria that contribute to the increased total bacterial load and/or reduced bacterial diversity in the airway of the subject having lung cancer. In some forms, the therapeutic (e.g., antibiotic) selectively targets, inhibits, kills or a combination thereof, one or more of the types of the bacteria enriched in the lung of a subject having lung cancer compared to a healthy subject.

The therapeutic (e.g., antibiotic) may selectively target, inhibit or kill pathogenic or non-pathogenic (e.g., commensal) bacteria in the lung. The bacterial community of the healthy lung is diverse. Studies characterizing the bacterial communities of the lung and general respiratory tract have been disclosed (e.g., Bassis, et al., *MBio.*, 6(2):e00037 (2015) and Dickson, et al.) and can be used to inform the types of bacteria that could be selectively targeted, inhibited or killed. The most abundant phyla in the lungs are Bacteroidetes, Firmicutes and Proteobacteria; prominent genera include *Prevotella, Veillonella, Streptococcus, Staphylococcus* and *Pseudomonas*. Any of the aforementioned bacterial phyla, genera or species may be altered in a diseased condition. For example, changes in the local microbial community have been associated with the exacerbation of some pulmonary disorders, including chronic obstructive pulmonary disease (COPD), asthma and cystic fibrosis (Albert, et al., *N. Engl. J. Med.*, 365:689-698 (2011); Gollwitzer, et al., *Nat. Med.*, 20:642-647 (2014); Marsland and Gollwitzer, *Nat. Rev. Immunol.*, 14:827-835 (2014)). In some forms, the relative abundance of Leuconostoceae, Sphingomonadaceae, Alphaproteobacteria, Herbaspirillum, Burkholderiales, or combinations thereof, is increased and/or enriched in tumor-bearing lungs. Bacteria may be increased or enriched in the lungs of a subject having cancer as compared to a healthy individual (see, e.g., WO2016097769), and as such, may be selectively targeted, inhibited or killed by the antimicrobial therapeutic (e.g., antibiotic). Accordingly, these bacteria may be selectively targeted, inhibited or killed by the antimicrobial therapeutic (e.g., antibiotic).

Generally, antibiotics can be grouped into different classes based on their chemical or pharmacologic properties. Their chemical structures may look comparable, and antibiotics within the same class may kill the same or related bacteria. Non-limiting examples of antibiotic classes suitable for use include aminoglycosides, ansaycins, carbapenems, cephalosporins, glycopeptides, lincosamides, lipopeptides, macrolides, monobactams, nitrofurans, oxazolidinones, penicillins, polypeptides, quinolones/fluoroquinolone, sulfonamides, tetracyclines, clofazimine, dapsone, capreomycin, cycloserine, ethambutol, ethionamide, isoniazid, pyrazinamide, rifampicin (rifampin), rifabutin, rifapentine, streptomycin, arsphenamine, chloramphenicol, fosfomycin, fusidic acid, mupirocin, platensimycin, quinupristin/dalfopristin, thiamphenicol, tigecycline, tinidazole, and trimethoprim.

More specifically, antibiotics suitable for use include antibiotics such as Ampicillin, Neomycin, Metronidazole, Vancomycin, Azithromycin, Clarithromycin, Clindamycin, Erythromycin, Aclacinomycins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin. In some forms, suitable antibiotics preferably include Ampicillin, Neomycin, Metronidazole, Vancomycin, Azithromycin, Clarithromycin, Clindamycin, and Erythromycin.

Depending on the range of bacterial species susceptible to these agents, antibiotics can be classified as broad-spectrum, intermediate-spectrum, or narrow-spectrum. Broad spectrum antibiotics are active against both Gram-positive and Gram-negative organisms. Examples of broad spectrum antibiotics include tetracyclines, phenicols, fluoroquinolones, "third-generation" and "fourth-generation" cephalosporins. Narrow spectrum or restricted spectrum antibiotics have more limited activity and are primarily only useful against particular species of bacteria (e.g., Gram-positive bacteria, Gram-negative bacteria, aerobic bacteria, anaerobic bacteria). For example, glycopeptides and bacitracin are only effective against Gram-positive bacteria, whereas polymixins are usually only effective against Gram-negative bacteria Aminoglycosides and sulfonamides are only effective against aerobic organisms, while nitroimidazoles are generally only effective for anaerobes. Preferably, in some forms, the antimicrobial is a restricted spectrum antibiotic. One of skill in the art would understand that the antibiotic to be used as a therapeutic would be selected based on the type of bacteria being preferentially targeted, inhibited or killed. For example, in some forms, a restricted spectrum antibiotic can be selected for administration because it can selectively target, inhibit, kill, or a combination thereof, one or more of the types of the bacteria enriched in the lungs of the subject or one or more of the types of the bacteria that contribute to the increased total bacterial load and/or reduced bacterial diversity in the lungs of the subject to be treated. Exemplary narrow-spectrum antibiotics suitable for use include Azithromycin, Clarithromycin, Clindamycin, Erythromycin, Vancomycin, and Metronidazole.

Patients suffering from cystic fibrosis (CF) often exhibit airway obstruction and chronic bacterial infection. Studies have shown that the airways of persons with CF may be inhabited by diverse bacterial communities composed of dozens of species including nonpathogenic oral bacteria, such as obligate and facultative anaerobic species. Antibiotic therapy of bacterial lung infections has contributed tremendously to the increased survival in CF. As such, antibiotic drugs used for the treatment of bacterial infections in patients having CF can also be used in accordance with the disclosed methods. See, for example, Chmiel et al., *Ann. Am. Thorac. Soc.*, 11(7):1120-9 (2014). Such antibiotic drugs can be used, for example, in methods of targeting the lung microbiota and its responding immune pathways in a subject in need thereof and/or in methods of treating cancer (e.g., lung cancer). Non-limiting examples of such antibiotics that can be used include Vancomycin, Linezolid, Tobramycin, Amikacin, Gentamicin, Colistin, Ticarcillin/clavulanate, Ceftazidime, Meropenem, Ciprofloxacin, Meropenem, Ceftazidime, Chloramphenicol, Trimethoprim/sulfamethoxazole, Aztreonam, Levofloxacin, Doxycycline, Tigecycline, Meropenem, Imipenem, Meripenem, Amoxicillin/clavulanate, Cephalexin, Cefdinir, Cefprozil, Cefaclor, Cefuroxime, Erythromycin/sulfisoxazole, Erythromycin, Clarithromycin, Azithromycin, Minocycline, Tetracycline, Methicillin, Oxacillin, Nafcillin, Cabenicillin, Ticarcillin, Piperacillin, Mezlocillin, Azlocillin, Cefepime, and combinations thereof.

In some forms, the antimicrobial (e.g., antibiotic) is formulated to be inhalable and/or aerosolized. In some forms, the antimicrobial (e.g., antibiotic) is formulated to be inhalable or aerosolized. In some forms, the antimicrobial (e.g., antibiotic) is formulated to be inhalable and aerosolized. In some forms, the antimicrobial (e.g., antibiotic) is in an inhalable or aerosolized form or formulation. The form or formulation may limit exposure of the antimicrobial (e.g., antibiotic) to a particular organ (e.g., the lung). This may avoid disrupting the microbiota in other regions/organs (e.g., the gut). In some forms, one or more antimicrobials (e.g., antibiotics) may be used in the disclosed methods of treatment. For example, any combination of more than one of the antibiotics listed above may be used.

B. Inhibitors of Immune Cells i. Tissue-resident Immune Cells

As demonstrated in the Examples, it has been discovered that lung tumor growth is associated with a dysregulation of the local microbiota. Specifically, it was observed that the local bacteria stimulated the proliferation and activation of lung-resident γδ T cells, which then produced a number of pro-inflammatory cytokines such as IL-17 that promoted neutrophil expansion and tumor cell proliferation. Thus, tissue-resident cells can be mediators of the pro-inflammatory and pro-tumorigenic effect of the local microbiota.

Generally, immune homeostasis at mucosal sites is maintained by tissue-resident immune cells that continually monitor the external environment, instructing tolerance to innocuous commensals while mounting efficient and rapid immune responses against invading pathogens (Lloyd and Marsland, Immunity, 46:549-561 (2017)). For example, within the lungs, a complex system of local immune pathways maintain homeostasis, and epithelial-macrophages are vital for maintenance of immune homeostasis within the respiratory tract.

The pulmonary epithelium provides a barrier between the outside environment and the internal tissues and provides vital first line host defense against noxious stimuli and pathogenic insults. Pulmonary epithelial cells are able to secrete a wide range of cytokines and chemokines, as well as being in intimate contact with cells of the immune system.

In health, the lungs are populated with a number of different macrophage populations. Those macrophages resident within the airway lumen (airway macrophages, AM) are long-lived cells derived from embryonic progenitors that colonize the airways soon after birth and self-renew under homeostatic conditions. Further populations of monocyte-derived macrophages are recruited to the lung during inflammatory conditions, but airway macrophages represent a first line of defense of the airways and maintain pulmonary immune homeostasis via their close interaction with other lung-resident cells, primarily pulmonary epithelial cells.

Although epithelial macrophage interactions facilitate first line defense of the airways; if appropriate a second tier of immune responses coordinated by local, tissue-resident lymphoid cells is elicited. This will then control the initiation of effector responses that mediate repair and resolution, and ultimately restitution of homeostasis. Lymphocytes circulate through the lung via the lymph, patrolling for potential antigen encounter. Specialized subsets of T cells are recruited to the lung following encounter with antigen. It is now clear that the lung harbors resident populations of both memory T cells and innate lymphoid cells, as well as other resident cells such as regulatory T cells and γδ T cells—all working collaboratively with the local dendritic cell network, thereby ensuring efficient triggering of both innate and memory responses. Also, regulatory T cells (Treg cells) are resident within lungs and are vital for maintenance of immune tolerance to airborne particles.

Under homeostatic conditions, the respiratory mucosa has an integrated network of dendritic cells (DC) largely comprising two conventional DC subsets and plasmacytoid DCs, each with distinct functions. In addition, upon inflammation, monocyte-derived inflammatory cells are recruited to the airways to facilitate the inflammatory response.

γδ T cells constitute a major tissue-resident T cell component of mucosal barrier tissues such as the gut, skin and lung. They display 'innate-like' characteristics and respond rapidly to infections and tissue damage (Papotto, et al., Nat. Immunol., 18:604-611 (2017); Vantourout and Hayday, Nat. Rev Immunol., 13:88-100 (2013)). In particular, IL-17-producing γδ T cells are thought to provide protective immunity to infections at mucosal sites. In the lung, γδ T cells form the first line of defense against various bacterial infections; however, prior to the present disclosure, γδ T cells had no known function(s) in lung cancer.

ii. Anti-immune Cell Therapeutic

As demonstrated in the Examples, it has been discovered that lung-resident γδ T cells have a previously unappreciated role of promoting tumorigenesis upon activation by local commensal bacteria in the airway. Disclosed herein is a novel mechanism whereby developing tumors in the lung, hijack tissue-resident or tumor-infiltrating lymphocytes to establish a pro-tumorigenic microenvironment in a manner dependent on the local microbiota.

Accordingly, disclosed are therapeutics which block or deplete tumor-infiltrating immune cells in a particular organ or tissue site for the treatment of cancer (e.g., lung cancer). In some forms, the therapeutics reduce cancer cell proliferation or viability and/or reduce tumor burden in the subject by reducing, blocking, or depleting a population of tumor-infiltrating immune cells in the affected area of the subject (e.g., the lung of a subject having lung cancer).

Tumor-infiltrating immune cells may include, but are not limited to, basophils, dendritic cells, eosinophils, Langerhans cells, mast cells, monocytes, macrophages, neutrophils, natural killer (NK) cells, and tissue-resident lymphocytes including γδ T cells. In the context of lung cancer for example, tumor-infiltrating immune cells may include, but are not limited to, airway macrophages and other monocyte-derived macrophages, T cells (e.g., memory T cells, regulatory T cells, γδ T cells), neutrophils, and dendritic cells (e.g., plasmacytoid DCs). Preferably, in some forms the tumor-infiltrating immune cells are γδ T cells and neutrophils. It is thought that microbiota can modulate the immune response by regulating activation/recruitment of immune and/or inflammatory cells from the circulation. Accordingly, in some forms, the tumor-infiltrating immune cells (e.g., γδ T cells and neutrophils) may be activated and/or proliferated by stimulation by the local microbiota (e.g., lung microbiota). Activated or proliferative tumor-infiltrating immune cells often exhibit markers indicative of this functional state. For example, γδ T cells may be positive for promyelocytic leukemia zinc finger (PLZF), CD27, CD44, CD69, or PD1. Accordingly, in some forms, the therapeutics block or deplete γδ T cells positive for promyelocytic leukemia zinc finger (PLZF), CD27, CD44, CD69, and/or PD1.

Therapeutics that block or deplete tumor-infiltrating immune cells (herein referred to as anti-immune cell therapeutic or immune cell inhibitor) could encompass any compound or entity, such as a small organic molecule, peptide or nucleic acid. For example, such anti-immune cell therapeutics may include small molecules, therapeutic polypeptides, antibodies, aptamers, inhibitory nucleic acids (e.g., miRNAs, piRNAs and siRNAs) or combinations thereof. Preferably, in some forms the anti-immune cell therapeutic is an antibody (e.g., an antibody against γδ T cells or neutrophils). A skilled person, based on methods known in the art, would understand how to generate a γδ T cell or neutrophil antibody. Such an antibody could target for example, a cell surface marker that is uniquely expressed by γδ T cells or neutrophils. Non-limiting examples of neutrophil specific markers include HNA-1a, HNA-1b, HNA-1c, and HNA-2a. Further identification of anti-neutrophil antibodies has been disclosed and such antibodies are commercially available (Bruin, et al., *Blood*, 94(5):1797-802 (1999)). In some forms, the antibody can target activated or proliferative tumor-infiltrating immune cells, such as γδ T cells positive for PLZF, CD27, CD44, CD69, and/or PD1.

Other immune cell inhibitors could be readily identified based on methods known in the art, such as, a small molecule screen for example. Using a similar approach, the antibiotic PF1052 was identified as a neutrophil inhibitor (Wang, et al, *Dis. Model Mech.*, 7(1):163-9 (2014)) and is contemplated herein for use as an immune cell inhibitor.

C. Inhibitors of Cytokines/Chemokines

The data in the examples demonstrate that cytokines or chemokines (including IL-1β, IL-23, IL-17, IL-22, amphiregulin and CXCL2) produced by immune cells in response to local microbiota, can promote inflammation and tumor development. Mechanistically, TLR ligands derived from the lung microbiota may stimulate the production of IL-1β and IL-23 from alveolar macrophages and neutrophils in a Myd88-dependent manner, and thereby induce proliferation and activation of lung-resident γδ T cells to further augment the inflammatory response. For example, it has been discovered that specifically blocking IL-17A or targeting IL22RA1 in the mouse model were both effective in suppressing tumor growth. As such, pharmacological inhibition of cytokines or chemokines and their downstream pathways can be developed for lung cancer treatment, for example, monoclonal antibodies for neutralizing the cytokines, or chemical compounds for blocking their receptors.

i. Cytokines

Cytokines are small, secreted proteins released by cells that have a specific effect on the interactions and communications between cells. Cytokine is a general name; other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on the cells that secrete them (autocrine action), on nearby cells (paracrine action), or in some instances on distant cells (endocrine action).

Cytokines are made by many cell populations, but the predominant producers are helper T cells (Th) and macrophages. It is common for different cell types to secrete the same cytokine or for a single cytokine to act on several different cell types (pleiotropy). Cytokines are redundant in their activity, meaning similar functions can be stimulated by different cytokines. They are often produced in a cascade, as one cytokine stimulates its target cells to make additional cytokines. There are both pro-inflammatory cytokines and anti-inflammatory cytokines. Cytokines can also act synergistically or antagonistically.

Cytokines typically act as hormonal regulators or signaling molecules at nano-to-picomolar concentrations. The cytokine can be a protein, peptide, or glycoprotein. Exemplary cytokines include, but are not limited to, interleukins (e.g., IL-1, IL-2, IL-4, IL-5, IL-6, IL-7, IL-10, IL-12, IL-15, IL-17, IL-21, IL-22, IL-23, etc.), interferons (e.g., IFN-α, IFN-γ), granulocyte macrophage colony stimulating factor (GM-CSF), granulocyte colony stimulating factor (G-CSF), tumor necrosis factor (e.g., TNF-α, TNF-β), Leukocyte Inhibitory Factor (LIF), lymphotactin (LTN), dendritic cell chemokine 1 (DC-CK1), SDF-1α, and chemokines.

ii. Chemokines

Chemokines are soluble, small molecular weight (8-14 kDa) proteins that bind to their cognate G-protein coupled receptors (GPCRs) to elicit a cellular response, usually directional migration or chemotaxis. Their name is derived from their ability to induce directed chemotaxis in nearby responsive cells. Therefore, they are chemotactic cytokines.

Proteins are classified as chemokines according to shared structural characteristics such as small size (they are all approximately 8-10 kDa in size), and the presence of four cysteine residues in conserved locations that are key to forming their 3-dimensional shape. Based on the positioning of the conserved two N-terminal cysteine residues of the chemokines, they are classified into four groups: CXC, CC, CX3C and C chemokines. The CXC chemokines can be further classified into ELR+ and ELR− chemokines based on the presence or absence of the motif 'glu-leu-arg (ELR motif)' preceding the CXC sequence. Chemokines induce cell signaling by binding to G protein-linked transmembrane receptors (i.e., chemokine receptors). The CXC chemokines bind to and activate their cognate chemokine receptors on neutrophils, lymphocytes, endothelial and epithelial cells. The CC chemokines act on several subsets of dendritic cells, lymphocytes, macrophages, eosinophils, natural killer cells but do not stimulate neutrophils as they lack CC chemokine receptors except murine neutrophils. There are approximately 50 chemokines and only 20 chemokine receptors, thus there is considerable redundancy in this system of ligand/receptor interaction.

Tumor cells secrete and respond to chemokines, which facilitate growth that is achieved by increased endothelial cell recruitment and angiogenesis, subversion of immunological surveillance and maneuvering of the tumoral leukocyte profile to skew it such that the chemokine release enables the tumor growth and metastasis to distant sites. Thus, chemokines are vital for tumor progression.

Chemokines elaborated from the tumor and the stromal cells bind to the chemokine receptors present on the tumor and the stromal cells. The autocrine loop of the tumor cells and the paracrine stimulatory loop between the tumor and the stromal cells facilitate the progression of the tumor. Notably, CXCR2, CXCR4, CCR2 and CCR7 play major roles in tumorigenesis and metastasis. CXCR2 plays a vital role in angiogenesis and CCR2 plays a role in the recruitment of macrophages into the tumor microenvironment. CCR7 is involved in metastasis of the tumor cells into the sentinel lymph nodes as the lymph nodes have the ligand for CCR7, CCL21. CXCR4 is mainly involved in the metastatic spread of a wide variety of tumors.

iii. Cytokine/Chemokine Inhibitors

Disclosed are therapeutics which locally inhibit one or more cytokines and/or chemokines or locally inhibit cytokine and/or chemokine activity in a particular organ or tissue site for the treatment of cancer (e.g., lung cancer). In some forms, the therapeutics reduce cancer cell proliferation or viability and/or reduce tumor burden in the subject by locally inhibiting one or more cytokines and/or chemokines, and/or cytokine and/or chemokine activity in the affected area of the subject (e.g., the lung of a subject having lung cancer). In some forms, the therapeutics may inhibit one or more of interleukins (e.g., IL-1, IL-1β, IL-2, IL-4, IL-5, IL-6, IL-7, IL-10, IL-12, IL-15, IL-17, IL-21, IL-22, IL-23, etc.), interferons (e.g., IFN-α, IFN-γ), granulocyte macrophage colony stimulating factor (GM-CSF), granulocyte colony stimulating factor (G-CSF), tumor necrosis factor (e.g., TNF-α, TNF-β), Leukocyte Inhibitory Factor (LIF), lymphotactin (LTN), dendritic cell chemokine 1 (DC-CK1), SDF-1α, TGF-β, amphiregulin, PTGS2, chemokines (e.g., CXC, CC, CX3C and C chemokines, including CXCL2), matrix metalloproteinases (MMPs), IL-1R1, IL-23R, and IL-22R. The therapeutics may directly inhibit any of the aforementioned, or their downstream effectors. For example, the therapeutic may decrease the synthesis of cytokines/chemokine, decrease their concentration in free active form, block their interaction with specific receptors, or interfere with the signaling of cytokine/chemokine receptors.

Therapeutics that inhibit cytokines/chemokines and/or their activity could encompass any compound or entity, such as a small organic molecule, peptide or nucleic acid. For example, such therapeutics may include small molecules, therapeutic polypeptides, antibodies, aptamers, inhibitory nucleic acids (e.g., miRNAs, siRNAs, shRNAs and piRNAs) or combinations thereof. Methods for designing and producing inhibitory nucleic acids such as miRNAs or siRNAs are well-known in the art and can be used. For example, predesigned siRNAs are commercially available through Dharmacon and can be used.

Preferably, in some forms the inhibitory therapeutic is an antibody (e.g., an antibody that neutralizes cytokines/chemokines). A skilled person, based on methods known in the art, would understand how to generate such an antibody. Further, anti-cytokine antibodies, such as for example, Infliximab, Certolizumab, Golimumab (anti-TNF antibodies), Tocilizumab (a recombinant, humanized, anti-IL-6R monoclonal antibody), and Canakinumab (a neutralizing monoclonal antibody targeted at IL-1β) are known in the art and are readily available. The aforementioned antibodies and other cytokine/chemokine inhibitors known in the art (for example, those disclosed in Rider, et al., *Int. J. Cell Biol.*, 2016:9259646 (2016); Siebert, et al., *Pharmacol. Rev.*, 67(2):280-309 (2015); Gabay C., *Expert Opin. Biol. Ther.*, 2(2):135-49 (2002); and Resch K., Cytokine Inhibitors. In: Vohr H W. (eds) Encyclopedic Reference of Immunotoxicology. Springer, Berlin, Heidelberg (2005)) are contemplated herein for use as an anti-cytokine/chemokine therapeutic. For example, in some forms, the therapeutic is canakinumab (anti-IL1beta), secukinumab (anti-IL17), ixekizumab (anti-IL17), brodalumab (anti-IL17RA), risankizumab (anti-IL23), guselkumab (anti-IL23), or tildrakizumab (anti-IL23).

D. Additional Active Agents

Each of the different therapeutics disclosed here can be administered alone or in any combination and further in combination with one or more additional therapeutic agents. In all cases, the combination of therapeutic agents can be part of the same admixture, or administered as separate compositions. In some forms, the separate compositions are administered through the same route of administration. In other forms, the separate compositions are administered through different routes of administration. As used herein, "combination" or "combined" refer to either concomitant, simultaneous, or sequential administration of the therapeutics. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

In some forms, the one or more therapeutics is one or more other targeted therapies (e.g., a targeted cancer therapy) and/or immune-checkpoint blockage agents. Examples of preferred additional active agents include other conventional therapies known in the art for treating the desired disease or condition. For example, for the treatment of lung cancer, the additional therapy may be Avastin, Afatinib, Alectinib, and/or combinations thereof.

i. Targeted Cancer Therapies

In the context of cancer, targeted therapies are therapeutic agents that block the growth and spread of cancer by interfering with specific molecules ("molecular targets") that are involved in the growth, progression, and spread of cancer. Targeted cancer therapies are sometimes called molecularly targeted drugs, molecularly targeted therapies, or precision medicines. Many different targeted therapies have been approved for use in cancer treatment. These therapies include hormone therapies, signal transduction inhibitors, gene expression modulators, apoptosis inducers, angiogenesis inhibitors, immunotherapies, and toxin delivery molecules. Exemplary lung cancer targeted therapies which may be used in accordance with the disclosed compositions and methods include, but are not limited to, Bevacizumab, crizotinib, erlotinib, gefitinib, afatinib dimaleate, ceritinib, ramucirumab, nivolumab, pembrolizumab, osimertinib, necitumumab, alectinib, atezolizumab, brigatinib, trametinib, dabrafenib, and durvalumab.

ii. Immune-checkpoint Blockage Agents

In some forms, the one or more therapeutics is an agent that prevents, reduces or inhibits the biological activity of one or more immune-suppressor molecules. Referred to as checkpoint blockade, this is a transformative therapeutic approach to a broad spectrum of malignancies because it increases the power of antitumor immunity to obtain durable responses. In some forms, the one or more therapeutics directly or indirectly targets, reduces or prevents expression of an immunosuppressive cell surface receptor, such as PDL-1, CTLA-4, TGF-β, TIM-3, VISTA, LAG-3, IDO, KIR or IL-10 (reviewed in Kamphorst, et al., *Vaccine* 33(0 2): B21-B28 (2015); Dempke, et al., *Eur J Cancer*, V74, p. 55-72 (2017)).

Exemplary antagonists of immune-suppressors include antibodies, small molecules and functional RNAs (e.g., siRNAs). In some forms, the one or more therapeutics is an antibody, or antigen-binding fragment thereof. Typically, the antibodies are monoclonal antibodies, formulated for administration via intravenous (iv) infusion. An exemplary dosage for humans is between 1 and 15 mg/kg body weight of the recipient. An exemplary concentration for administration to humans is between 1 and 20 mg/ml. Exemplary monoclonal antibodies include anti-CTLA-4, and anti-PD1/PDL1 antibodies.

a. Antagonists of CTLA-4

In some forms, the one or more therapeutics directly or indirectly targets, reduces, or prevents the expression and/or function of Cytotoxic T-lymphocyte-associated antigen 4 (CTLA-4). CTLA-4 is expressed on the surface of T cells, where it primarily suppresses their early stages of activation by inducing inhibitory downstream T-cell receptor (TCR) signaling and counteracting activity of the T-cell costimulatory receptor, CD28. CTLA-4 is an inhibitory co-receptor that binds with higher affinity to B7 ligands than CD28. CTLA-4 is induced by TCR signaling, and it competes and physically excludes CD28 from the immunological synapse. In addition, CTLA-4 also recruits phosphatases that dephosphorylate key TCR/CD28 signaling molecules. In some forms, the one or more therapeutics is an anti-CTLA-4 antibody (e.g., Ipilimumab and Tremelimumab).

b. Antagonists of PD-1

In some forms, the one or more therapeutics directly or indirectly targets, reduces, or prevents the expression and/or function of programmed death-1 receptor (PD-1, CD279), and/or its ligand binding partners (e.g., PD-L1 (B7-H1, CD274) and PD-L2 (B7-DC, CD273)). PD-1 is related to CD28 and CTLA-4, but lacks the membrane proximal cysteine that allows homodimerization. PD-1 is expressed on a subset of thymocytes and up-regulated on T, B, and myeloid cells after activation (Agata, et al., *Int. Immunol.*, 8:765-772 (1996)). PD-1 is an inhibitory receptor that modulates TCR and CD28 signaling through recruitment of the phosphatase SHP2. PD-1 binds PD-L1 (B7-H1/CD274) and PD-L2 (B7-DC/CD273). PD-L2 expression is restricted to antigen presenting cells (dendritic cells, monocytes and some B cell subsets), but PD-L1 expression is widespread. Expression of both PD-1 ligands is modulated by cytokines, such as IFN-γ. PD-L1 is expressed on hematopoietic and non-hematopoietic cells, including many tumor cells. PD-1 acts to antagonize signal transduction downstream of the TCR after it binds a peptide antigen presented by the major histocompatibility complex (MHC). It can function as an immune checkpoint, by preventing the activation of T-cells, which in turn reduces autoimmunity and promotes self-tolerance, but can also reduce the body's ability to combat cancer. The inhibitory effect of PD-1 acts through a twofold mechanism: promoting apoptosis (programmed cell death) in antigen specific T-cells in lymph nodes and simultaneously reducing apoptosis in regulatory T cells (suppressor T cells). Blocking interactions of PD-1 with PD-L1 can improve primary T cell responses and can activate the immune system to attack tumors. In some forms, the one or more therapeutics is an anti-PD-1 or anti-PD-L1 antibody. Anti-PD-L1 antibodies and antigen-binding fragments thereof suitable for use are known in the art and include atezolizumab, avelumab, durvalumab, pembrolizumab, nivolumab and antibodies disclosed in U.S. Pat. No. 9,624, 298, which is hereby incorporated by reference in its entirety.

iii. Other Chemotherapeutics

Numerous antineoplastic drugs are available for combination with the disclosed therapeutics. In some forms, the one or more therapeutics is a chemotherapeutic or antineoplastic drug. The majority of chemotherapeutic drugs can be divided into alkylating agents, antimetabolites, anthracyclines, plant alkaloids, topoisomerase inhibitors, monoclonal antibodies, and other antitumour agents.

Exemplary additional anticancer agents that can be used as the one or more therapeutics in accordance with the disclosed methods include, but are not limited to, gefitinib, erlotinib, cis-platin, 5-fluorouracil, tegafur, raltitrexed, cytosine arabinoside, hydroxyurea, adriamycin, bleomycin, daunomycin, mitomycin-C, dactinomycin and mithramycin, vincristine, vinblastine, vindesine, vinorelbine, etoposide, etoposide phosphate, teniposide, camptothecins such as irinotecan and topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, dacarbazine, oxaliplatin, procarbazine, temozolomide, valrubicin, actinomycins such as actinomycin D, trastuzumab (HERCEPTIN®), bevacizumab (AVASTIN®), gemtuzumab (MYLOTARG®), panitumumab (VECTIBIX®) or edrecolomab (PANOREX®), tyrosine kinase inhibitor, such as sorafenib (NEXAVAR®) or sunitinib (SUTENT®), cetuximab, dasatinib, imatinib, combretastatin, thalidomide, and/or lenalidomide, alkylating agents; alkyl sulfonates; aziridines, such as Thiotepa; ethyleneimines; anti-metabolites; folic acid-analogues, such as methotrexate (FARMITREXAT®, LANTAREL®, METEX®, MTX HEXAL®); purine analogues, such as azathioprine (AZAIPRIN®, AZAMEDAC®, IMUREK®, Zytrim®), cladribin (LEU-STATIN®), fludarabin phosphate (Fulda®), mercapto purine (MERCAP®, PURI-NETHOL®), pentostatin (NIPENT®), thioguanine (THIO-GUANIN-WELLCOME®) or fludarabine; pyrimidine analogues, such as cytarabin (ALEXAN®, ARA-CELL®, UDICIL®), fluorouracil, 5-FU (EFUDIX®, FLUORO-BLASTIN®, RIBOFLUOR®), gemcitabine (GEMZAR®), doxifluridine, azacitidine, carmofur, 6-azauridine, floxuridine; nitrogen-lost-derivatives, such as chlorambucil (LEUKERAN®), melphalan (ALKERAN®), chlornaphazine, estramustin, mechlorethamine; oxazaphosphorines, such as cyclophosphamide (CYCLO-CELL®, CYCLOSTIN®, ENDOXAN®), ifosfamide (HOLOXAN®, IFO-CELL®) or trofosfamide (IXOTEN®); nitrosureas, such as Bendamustine (RIBOMUSTIN®), Carmustine (CARMUBRIS®), Fotemustine (MUPHORAN®), Lomustine (CECENU®, LOMEBLASTIN®), chlorozotocine, ranimustine or nimustine (ACNU®); hydroxy-ureas (LITALIR®); taxens, such as docetaxel (TAXOTERE®), or paclitaxel (TAXOL®); platinum-compounds, such as cisplatin (PLATIBLASTIN®, PLATINEX®) or carboplatin (CARBOPLAT®, RIBOCARBO®); sulfonic acid esters, such as busulfan (MYLERAN®), piposulfan or treosulfan (OVASTAT®); anthracyclines, such as doxorubicin (ADRIBLASTIN®, DOXO-Cell®), daunorubicin (DAUNOBLASTIN®), epirubicin (FARMORUBICIN®), idarubicin (ZAVEDOS®), amsacrine (AMSIDYL®) or Mitoxantrone (NOVANTRON®); as well as derivates, tautomers and pharmaceutically active salts of the aforementioned compounds.

III. Methods

A. Methods of Targeting Lung Microbiota and Immune Pathways

Methods of using the compositions are provided, particularly for targeting the lung microbiota and its responding immune pathways in a subject having lung cancer and/or for treating cancer (e.g., lung cancer). Targeting the lung microbiota and its responding immune pathways encompasses strategies that selectively and/or preferentially, but not necessarily exclusively, effect an impact (e.g., blockade, reduction, inhibition, depletion) on the local lung microbiota and the downstream cellular or molecular immune mediators. In some forms, the downstream cellular or molecular immune mediators include, but are not limited to, macrophages, neutrophils, T cells, cytokines and chemokines such as, IL-1β, IL-23, IL-17, IL-22, amphiregulin, and CXCL2. In preferred forms, these strategies effect an impact on local (e.g., lung) but not distal (e.g., gut) microbiota.

The methods typically include administering to a subject in a need thereof an effective amount of one or more compositions including one or more therapeutics. The one or more therapeutics may reduce the local bacterial load, block or deplete tumor-infiltrating immune cells, locally inhibit one or more cytokines or chemokines, or a combination thereof. In some forms, the administration of the therapeutics reduces cancer cell proliferation or viability and/or reduces tumor burden in the subject. In some forms, the reduction in the local bacterial load, block or depletion of tumor-infiltrating immune cells, local inhibition of one or more cytokines or chemokines, or a combination thereof, reduces cancer cell proliferation or viability and/or reduces tumor burden in the subject.

The one or more therapeutics may reduce cancer cell proliferation or viability and/or reduce tumor burden in the subject. These effects on cell proliferation or viability or tumor burden can be direct (e.g., not mediated through an intermediate) or indirect (e.g., effects of the therapeutic are mediated through one or more intermediates, e.g., a cell or signaling molecule). In some forms, the one or more therapeutics may lead to direct, and/or indirect reduction of tumor cell proliferation by 5%, 10%, 20%, 30%, 40%, 50%, 60%, 70%, 80%, 90%, or more than 90%. In some forms, the one or more therapeutics may lead to direct, and/or indirect reduction of cancer cell viability by 5%, 10%, 20%, 30%, 40%, 50%, 60%, 70%, 80%, 90%, or more than 90%. In some forms, the one or more therapeutics may lead to direct, and/or indirect reduction in tumor burden by 5%, 10%, 20%, 30%, 40%, 50%, 60%, 70%, 80%, 90%, or more than 90%. It is to be understood that the aforementioned reductions are relative to a control, which need not be stated. One of ordinary skill in the art can determine the appropriate control. For example, in some forms, reduction is relative to a state prior to administration of the one or more therapeutics. In some forms, reduction is relative to a subject who is not administered the one or more therapeutics.

In some forms, the therapeutics reduce the local bacterial load in the lungs. In some forms, the therapeutics block or deplete tumor-infiltrating immune cells in an affected organ or tissue. In some forms, the therapeutics locally inhibit one or more cytokines and/or chemokines or locally inhibit cytokine and/or chemokine activity in an affected organ or tissue. In some forms, the one or more therapeutics may reduce cancer cell proliferation or viability and/or reduce tumor burden through any combination of the foregoing.

It has been discovered that commensal bacteria, which are otherwise non-pathogenic and colonize pulmonary tissue at a much lower density in healthy individuals, could provoke chronic inflammation and disease exacerbation in the context of lung cancer. Therefore, in particular forms, the method of targeting the lung microbiota and its responding immune pathways in a subject having lung cancer and/or treating a cancer, such as lung cancer for example, involves (i) local administration of an effective amount of one or more therapeutics instead of systemic delivery, (ii) use of selective therapeutics, such as antibiotics for example, with restricted anti-microbial spectrum to target specific microbes (e.g., bacteria) enriched in a patient's lung, (iii) administering the therapeutics to subjects or patients who do not manifest the standard clinical symptoms of infection, or combinations thereof. In some forms, standard clinical symptoms of infection refers to symptoms that would indicate to the appropriate clinician (e.g., a physician) that the subject has an infection. For example, standard clinical symptoms of infection encompass symptoms from which an attending physician would conclude that a patient has an infection, such as a bacterial or fungal infection. In the case of a lung infection for example, such symptoms include, without limitation, production of brown, yellow, or green colored phlegm; sever cough; chest pain; fever; sweating; chills; dehydration; headache; shortness of breath; wheezing; bibasilar crackles; and combinations thereof.

Also disclosed are methods of treating a subject/patient sub-population by administration of one or more therapeutics in accordance with the provided methods. In some forms, a subject identified as having increased total bacterial load and/or reduced bacterial diversity compared to a healthy subject is administered one or more therapeutics in accordance with the provided methods. In some forms, a subject identified as having one or more types of bacteria enriched in an affected tissue (e.g., lung) compared to a healthy subject is administered one or more therapeutics in accordance with the provided methods. In some forms, a subject that does not manifest the standard clinical symptom(s) of infection (for example, the attending physician would conclude that the subject does not have a bacterial infection) is administered one or more therapeutics in accordance with the provided methods.

i. Effective Amounts

The effective amount or therapeutically effective amount can be a dosage sufficient to treat, inhibit, or alleviate one or more symptoms of a disease or disorder, or to otherwise provide a desired pharmacologic and/or physiologic effect, for example, reducing, inhibiting, or reversing one or more of the underlying pathophysiological mechanisms underlying a disease or disorder such as cancer.

Because the administration of the one or more therapeutics can elicit, for example, a reduction in the local bacterial load, a block or depletion of tumor-infiltrating immune cells, a local inhibition of one or more cytokines or chemokines, or a combination thereof, the amount administered can be expressed as the amount effective to achieve the desired effect in the recipient. For example, in some forms, the amount of the one or more therapeutics is effective to reduce the local bacterial load, to block or deplete tumor-infiltrating immune cells, to locally inhibit one or more cytokines or chemokines, or a combination thereof, in the recipient. In some forms, the amount of the one or more therapeutics is effective to reduce the local bacterial load in the recipient. In some forms, the amount of the one or more therapeutics is effective to block or deplete tumor-infiltrating immune cells in the recipient. In some forms, the amount of the one or more therapeutics is effective to inhibit (e.g., locally inhibit) one or more cytokines or chemokines in the recipient.

In some forms, the administration of the one or more therapeutics elicits an anti-cancer response, the amount administered can be expressed as the amount effective to achieve a desired anti-cancer effect in the recipient. For example, in some forms, the amount of the one or more therapeutics is effective to inhibit the viability or proliferation of cancer cells in the recipient. In some forms, the amount of the one or more therapeutics is effective to reduce the tumor burden in the recipient, or reduce the total number of cancer cells, and combinations thereof. In other forms, the amount of the one or more therapeutics is effective to reduce one or more symptoms or signs of cancer in a cancer patient. Signs of cancer may include cancer markers, such as PSMA levels in the blood of a patient.

The effective amount of the compositions containing the therapeutics required will vary from subject to subject, depending on the species, age, weight and general condition of the subject, the severity of the disorder being treated, and its mode of administration. Thus, it is not possible to specify an exact amount for every therapeutic composition. However, an appropriate amount can be determined by one of ordinary skill in the art using only routine experimentation given the teachings herein. For example, effective dosages and schedules for administering the therapeutics may be determined empirically, and making such determinations is within the skill in the art. The dosage ranges for the administration of the compositions are those large enough to effect reduction in the local bacterial load, block or depletion tumor-infiltrating immune cells, inhibition (e.g., local inhibition) of one or more cytokines or chemokines, or a combination thereof, for example. As another example, the dosage ranges for the administration of the compositions are those large enough to effect reduction in cell proliferation or viability in target cells, or to reduce tumor burden for example.

The dosage should not be so large as to cause adverse side effects, such as unwanted cross-reactions, anaphylactic reactions, and the like. Generally, the dosage will vary with the age, condition, and sex of the patient, route of administration, whether other drugs are included in the regimen, and the type, stage, and location of the cancer to be treated. The dosage can be adjusted by the individual physician in the event of any counter-indications. It will also be appreciated that the effective dosage of the composition used for treatment may increase or decrease over the course of a particular treatment. Changes in dosage may result and become apparent from the results of diagnostic assays.

Dosage can vary, and can be administered in one or more dose administrations daily, for one or several days. Guidance can be found in the literature for appropriate dosages for given classes of pharmaceutical products. Optimal dosing schedules can be calculated from measurements of drug accumulation in the body of the subject or patient. Persons of ordinary skill can easily determine optimum dosages, dosing methodologies and repetition rates. Optimum dosages may vary depending on the relative potency of individual therapeutics, and can generally be estimated based on $EC_{50}$s found to be effective in in vitro and in vivo animal models.

Dosage levels on the order of about 1 mg/kg to 100 mg/kg of body weight per administration are useful in the treatment of a disease such as cancer. For example, in some forms, the dosage levels are about 10 mg/kg-50 mg/kg of body weight per administration. A typical daily dosage of an antibody used alone might range from about 1 μg/kg to up to 100 mg/kg of body weight or more per day, depending on the factors mentioned above. In some forms, the antibody is present in amount from about 200 mg/m$^2$ to about 1000 mg/m$^2$, more preferably from about 200-900, 300-800, 400-700, 500-600 mg/m$^2$. In some forms, the amount of a therapeutic agent administered is between about 1 mg and 1,000 mg, for example, between 10 mg and 500 mg, between 20 mg and 100 mg. In some forms, the unit dosage is in a unit dosage form for intravenous injection. In some forms, the unit dosage is in a unit dosage form for oral administration. In some forms, the unit dosage is in a unit dosage form for inhalation. In some forms, the unit dosage is in a unit dosage form for intratumoral injection.

Treatment can be continued for an amount of time sufficient to achieve one or more desired therapeutic goals, for example, a reduction of the amount of cancer cells relative to the start of treatment, or complete absence of cancer cells in the recipient. Treatment can be continued for a desired period of time, and the progression of treatment can be monitored using any means known for monitoring the progression of anti-cancer treatment in a patient. In some forms, administration is carried out every day of treatment, or every week, or every fraction of a week. In some forms, treatment regimens are carried out over the course of up to two, three, four or five days, weeks, or months, or for up to 6 months, or for more than 6 months, for example, up to one year, two years, three years, or up to five years.

The efficacy of administration of a particular dose of the therapeutics or compositions according to the methods described herein can be determined by evaluating the particular aspects of the medical history, signs, symptoms, and objective laboratory tests that are known to be useful in evaluating the status of a subject in need for the treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious. In some forms, efficacy is assessed as a measure of the reduction in tumor volume and/or tumor mass at a specific time point (e.g., 1-5 days, weeks or months) following treatment.

ii. Modes of Administration

Any of the disclosed therapeutic agents (also referred to as therapeutics) can be used therapeutically in combination with a pharmaceutically acceptable carrier. The therapeutics described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the therapeutics described herein and which is incorporated by reference herein. These most typically would be standard carriers for administration of compositions to humans. In one aspect, for humans and non-humans, these include solutions such as sterile water, saline, and buffered solutions at physiological pH. Other therapeutics will be administered according to standard procedures used by those skilled in the art.

The pharmaceutical compositions described herein can include, but are not limited to, carriers, thickeners, diluents, buffers, preservatives, surface active agents and the like in addition to the therapeutic(s) of choice.

Pharmaceutical compositions containing one or more therapeutics can be administered to the subject in a number of ways depending on whether local or systemic treatment is desired, and on the area to be treated. Thus, for example, a pharmaceutical composition can be administered as an ophthalmic solution and/or ointment to the surface of the eye. Moreover, a pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. The compositions may be administered directly into a tumor or tissue, e.g., stereotactically.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intra-retinal injection, or sub-retinal injection); subcutaneous injection or deposition including subcutaneous infusion (such as by osmotic pumps); direct application by a catheter or other placement device (e.g., an implant comprising a porous, non-porous, or gelatinous material).

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Pharmaceutical compositions containing one or more therapeutics for oral administration can include powders or granules, suspensions or solutions in water or non-aqueous media, capsules, sachets, or tablets. Thickeners, flavorings, diluents, emulsifiers, dispersing aids or binders may be desirable.

Administration of the pharmaceutical compositions containing one or more therapeutics may be localized (i.e., to a particular region, physiological system, tissue, organ, or cell type) or systemic. Preferably, pharmaceutical compositions containing one or more therapeutics are administered locally, e.g., administration by inhalation of a lyophilized powder. Such administration routes and appropriate formulations are generally known to those of skill in the art.

a. Preferred Formulations for Mucosal and Pulmonary Administration

Therapeutic agents (also referred to as therapeutics) and compositions thereof can be formulated for pulmonary or mucosal administration. The administration can include delivery of the composition to the lungs. In appropriate cases, the administration can include delivery of the composition to the nasal, oral (sublingual, buccal), vaginal, or rectal mucosa. Such modes of administration are particularly advantageous in the treatment of lung cancer and/or targeting lung microbiota and its responding immune pathways in accordance with the disclosed methods, where local reduction of bacterial load, blockade or depletion of tumor-infiltrating immune cells, or local inhibition of one or more cytokines and/or chemokines may be desirable.

In some forms, the therapeutics are formulated into pharmaceutical compositions for pulmonary delivery, such as intranasal administration or oral inhalation. Preferably, the pharmaceutical compositions with the therapeutic(s) is inhalable or aerosolized. For example, the disclosed methods of cancer treatment and/or targeting lung microbiota and its responding immune pathways may include (i) local administration of an effective amount of a therapeutic in an inhalable or aerosolized form or formulation, (ii) use of selective therapeutics, such as antibiotics for example, with restricted anti-microbial spectrum to target specific bacteria enriched in a subject's or patient's lung, (iii) administering the therapeutics to subjects or patients who do not manifest the standard clinical symptoms of infection, or combinations thereof. In some forms, the pharmaceutical compositions with the therapeutic(s) is in an inhalable and/or aerosolized form or formulation. In some forms, the pharmaceutical compositions with the therapeutic(s) is in an inhalable or aerosolized form or formulation. In some forms, the pharmaceutical compositions with the therapeutic(s) is in an inhalable and aerosolized form or formulation.

The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

Carriers for pulmonary formulations can be divided into those for dry powder formulations and for administration as solutions. Aerosols for the delivery of therapeutics to the respiratory tract are known in the art. The term aerosol as used herein refers to any preparation of a fine mist of particles, which can be in solution or a suspension, whether or not it is produced using a propellant. Aerosols can be produced using standard techniques, such as ultrasonication or high-pressure treatment. Inhalable as used herein includes the state of being deliverable to the airway (e.g., respiratory tract, lungs). The inhaled route allows the delivery of a therapeutic directly to the airway achieving a high local concentration while minimizing systemic delivery and/or adverse effects. As a result, considerably lower inhaled doses can be therapeutically equivalent or even superior to higher doses of systemically administered therapy. An inhalable form or formulation may contain a powder, liquid particles, or solid particles of the therapeutic of a size sufficiently small to pass through the mouth and larynx upon inhalation and continue into the bronchi and alveoli of the lungs. Aerodynamic particle size determines deposition patterns across the human respiratory tract. Smaller particles generally deposit more peripherally in the lung, such as in the alveolar space, whereas larger particles deposit more centrally, for example, in the large conducting airways (Borghardt J M., et al., Can. Respir. J., 2018:2732017). One skilled in the art can readily optimize particle size to achieve specific airway delivery of an inhalable therapeutic. For administration via the upper respiratory tract, the pharmaceutical composition can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In other forms, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

The pharmaceutical compositions may contain minor amounts of polymers, surfactants, or other excipients well known to those of the art. In this context, "minor amounts" means no excipients are present that might affect or mediate uptake of the therapeutics in the lungs and that the excipients that are present are present in amount that do not adversely affect uptake of compounds in the lungs.

iii. Cancers to be Treated

Cancer is a disease of genetic instability, allowing a cancer cell to acquire the hallmarks proposed by Hanahan and Weinberg, including (i) self-sufficiency in growth signals; (ii) insensitivity to anti-growth signals; (iii) evading apoptosis; (iv) sustained angiogenesis; (v) tissue invasion and metastasis; (vi) limitless replicative potential; (vii) reprogramming of energy metabolism; and (viii) evading immune destruction (*Cell.,* 144:646-674, (2011)).

Tumors which may be treated in accordance with the disclosed methods are classified according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The disclosed compositions and methods of treatment thereof are generally suited for treatment of carcinomas, sarcomas, lymphomas and leukemias. The described compositions and methods are useful for treating, or alleviating subjects having benign or malignant tumors by delaying or inhibiting the growth/proliferation or viability of tumor cells in a subject, reducing the number, growth or size of tumors, inhibiting or reducing metastasis of the tumor, and/or inhibiting or reducing symptoms associated with tumor development or growth.

The types of cancer that can be treated with the provided compositions and methods include, but are not limited to, cancers such as vascular cancer, myeloma, adenocarcinomas and sarcomas, of bone, bladder, brain, breast, cervical, colorectal, esophageal, kidney, liver, lung, nasopharangeal, pancreatic, prostate, skin, stomach, and uterine. In some forms, the compositions are used to treat multiple cancer types concurrently. The compositions can also be used to treat metastases or tumors at multiple locations.

Exemplary tumor cells include, but are not limited to, tumor cells of cancers, including leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, and carcinosarcoma. For a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In some forms, the cancer(s) to be treated is characterized as being a triple negative cancer, or having one or more KRAS-mutations, p53 mutations, EGFR mutations, ALK mutations, RB1 mutations, HIF mutations, KEAP mutations, NRF mutations, or other metabolic-related mutations, or combinations thereof.

Preferably, the cancer to be treated is a lung cancer such as small cell or non-small cell lung cancer (including adenocarcinoma, squamous cell carcinoma, and large cell carcinoma). In some forms, the cancer to be treated in accordance with the disclosed methods is lung adenocarcinoma. In some forms, the cancer to be treated in accordance with the disclosed methods is lung adenocarcinoma harboring KRAS-mutations and/or p53 mutations.

B. Microbial Analysis

Also disclosed are methods of analyzing the bacterial compositions in a sample from a subject. This analysis can be performed individually as a stand-alone method, or in conjunction with the method of treatments disclosed herein. For example, a method of treating cancer can involve analyzing the bacterial composition in a sample from the subject and administering an effective amount of one or more therapeutics to the subject. These steps may be performed in any order and/or repeatedly, either individually or in combination. For example, in some forms, a method of treating cancer can involve analyzing the bacterial composition in a sample from the subject prior to the administration of an effective amount of one or more therapeutics to the subject. In some forms, methods of targeting the lung microbiota and its responding immune pathways in a subject having lung cancer can involve analyzing the bacterial composition in a sample from the subject prior to the administration of an effective amount of one or more therapeutics to the subject. In other forms, the bacterial composition is analyzed after the administration of one or more therapeutics to the subject The sample from which the bacterial composition is analyzed can be any sample suitable for providing sufficient quantities for qualitative and/or quantitative assessment of the microbiome. The term "sample" refers to a specimen obtained from a subject and includes fluids, gases and solids including for example, tissue. In the context of the lungs or respiratory tract, the sample can be, for example, an oral wash, sputum sample, bronchoscopy biopsy, bronchoalveolar lavage (BAL) fluid, or nasal swab. Preferably, the samples is a sputum sample or bronchoscopy biopsy.

Sputum is a complex of mucus, pathogens, cellular debris and other particles trapped in the lungs. Increased sputum is a key symptom in many inflammatory lung airway diseases such as COPD, asthma, chronic bronchitis, and cystic fibrosis. Sputum has also been used to investigate microbial profiles in diseases including asthma, COPD and cystic fibrosis, to reveal important insights into the role that microbes may play in disease etiology, progression and treatment. It provides a noninvasive method of obtaining upper respiratory tract samples, and involves minimal patient discomfort. An example of how to obtain a sputum sample from a subject by non-invasive means is coughing. This is a rapid expulsion of air from the lungs, typically in order to clear the lung airways of fluids, mucus, or other material, also known as tussis.

Also described herein are invasive means of obtaining the sample from the subject. The methods include but are not limited to taking bronchoalveolar lavage fluid (the washing of the lungs with saline solution through bronchoscopy), taking of a biopsy of suspected cancerous tissue via a bronchoscopy, the taking of a blood sample from a patient, or the taking of a sputum sample through an induced method via the use of a hypertonic ultrasonic nebulizer.

As will be appreciated by those in the art, any experimental manipulation or sample preparation steps may be performed on the sample. For example, wash steps and/or fragmentation may be applied to a sample.

Molecular techniques of microbial identification are well known in the art (see for example, Dickson et al., and Hamady and Knight, *Genome Res.*, 19:1141-52 (2009)). Components of the microbiome, such as the bacterial composition, can be detected in a test sample using any of these known methods, including for example, microbial culture and/or detection of chromosomal DNA, or 16S rRNA profiling.

The most commonly used modern approach to the study of bacterial communities employs high-throughput sequencing of amplicons of the 16S rRNA gene, a small and highly conserved locus of the bacterial genome. When sequenced using platforms such as 454 pyrosequencing and Illumina MiSeq, DNA isolated from a single specimen yields thousands of short genome sequences. These sequences are aligned, sorted, and classified according to publicly available taxonomic databases. Sequences are clustered by similarity; by convention, sequences sharing 97% homology are grouped as operational taxonomic units (OTUs), which are roughly comparable to genus- or species-level phylogeny. The result of this bioinformatic analysis is a population census for each specimen: a tally of how many times each taxonomic group was counted. Comparisons in total bacterial abundance (using quantitative PCR), relative abundance (how much of a specimen's community is composed of a single taxonomic group), and community features (such as diversity) can be made across specimens. These sequencing-based techniques do not rely upon the reproduction of microbes in the narrow growth conditions of conventional culture techniques, which may fail to identify most human-associated microbes.

The level of bacterial species may be measured by taking a percentage abundance reading of the species present in the test sample as a total. Percentage abundance readings are useful as they provide data to perform accurate statistical analyses of the bacterial metagenomic data as a whole. In some forms, the level of bacterial species present in the test sample may be determined relative to a control sample. This would allow a comparison to be made between the levels of bacterial species in the lung microbiome in lung cancer subjects and the level in healthy subjects.

The disclosed methods of microbial analysis allow for determination of the presence and level of various bacterial species in a tissue or organ affected by a cancer. These methods could be helpful in identifying a number of bacterial species that may exhibit higher abundance in a subject having a disease or disorder such as lung cancer, compared to a healthy subject. This may be advantageous, for example in informing a medical practitioner as to which subset of bacteria should be preferentially targeted for treatment, and subsequently, the type of one or more therapeutics that should be used. For example, based on microbial analysis, certain anaerobic bacteria may be identified as being more abundant or enriched in a diseased subject compared to a healthy subject. In this case, a restricted spectrum antimicrobial such as metronidazole may be an appropriate therapeutic.

In some forms, a subject is identified as having increased total bacterial load and/or reduced bacterial diversity compared to a healthy subject. In some forms, a subject is identified as having one or more types of bacteria enriched in an affected tissue (e.g., lung) compared to a healthy subject. In some forms, the subject does not manifest the standard clinical symptom(s) of infection (for example, the attending physician would conclude that the subject does not have a bacterial infection). For example, a subject identified as having increased total bacterial load and/or reduced bacterial diversity, or having one or more types of bacteria enriched in their lungs compared to a healthy subject may not manifest the standard clinical symptom(s) of infection. Notwithstanding the above, the disclosed treatment can be administered to subjects with lung cancer that do not exhibit, or have not been tested for, any of these features. This is based on the prophylactic benefit of forestalling the effects of the subject's microbiota on the course of lung cancer.

The disclosed compositions and methods can be further understood through the following numbered paragraphs.

1. A method of targeting the lung microbiota and its responding immune pathways in a subject having lung cancer, the method comprising, administering to the subject an effective amount of one or more therapeutics, wherein the administration of the therapeutics reduces the local bacterial load, blocks or depletes tumor-infiltrating immune cells, locally inhibits one or more cytokines or chemokines, or a combination thereof.

2. A method of treating lung cancer in a subject having lung cancer, the method comprising, administering to the subject an effective amount of one or more therapeutics, wherein the administration of the therapeutics reduces cancer cell proliferation or viability and/or reduces tumor burden in the subject.

3. The method of paragraph 1 or 2, wherein the administration of the therapeutics reduces the local bacterial load in the lungs.

4. The method of any one of paragraphs 1-3, wherein the administration of the therapeutics blocks or depletes tumor-infiltrating immune cells in the lungs.

5. The method of any one of paragraphs 1-4, wherein the administration of the therapeutics locally inhibits one or more cytokines and/or chemokines or locally inhibits cytokine and/or chemokine activity in the lungs.

6. The method of any one of paragraphs 1-5, wherein, prior to the administration of the therapeutics, the subject does not manifest the standard clinical symptoms of infection.

7. The method of any one of paragraphs 1-6 further comprising, prior to the administration of the therapeutics, analyzing the bacterial composition in a sample from the subject.

8. The method of paragraph 7, wherein the sample is a sputum sample or bronchoscopy biopsy.

9. The method of paragraph 7 or 8, wherein the analysis comprises microbial culture and 16S-based sequencing.

10. The method of any one of paragraphs 7-9, wherein the subject is identified as having increased total bacterial load and/or reduced bacterial diversity compared to a healthy subject.

11. The method of any one of paragraphs 7-10, wherein the subject is identified as having one or more types of bacteria enriched in the lungs of the subject compared to a healthy subject.

12. The method of paragraph 11, wherein the one or more types of bacteria are commensal bacteria from groups such as the Leuconostoceae, Sphingomonadaceae, Alphaproteobacteria, Herbaspirillum, Burkholderiales, and combinations thereof.

13. The method of paragraph 11 or 12, wherein one or more of the therapeutics selectively targets, inhibits, kills, or a combination thereof, one or more of the types of the bacteria enriched in the lungs of the subject.

14. The method of any one of paragraphs 11-13, wherein one or more of the therapeutics is selected for administration because it can selectively target, inhibit, kill, or a combination thereof, one or more of the types of the bacteria enriched in the lungs of the subject.

15. The method of any one of paragraphs 4-14, wherein the immune cells are γδ T cells, neutrophils, or a combination thereof.

16. The method of paragraph 15, wherein the γδ T cells, neutrophils, or both were activated and/or proliferated by stimulation by lung microbiota of the subject.

17. The method of paragraphs 15 or 16, wherein the γδ T cells are positive for promyelocytic leukemia zinc finger (PLZF), CD27, CD44, CD69, and/or PD1.

18. The method of any one of paragraphs 5-17, wherein the one or more cytokines and/or chemokines comprise one or more of IL-1β, IL-23, IL-17, IL-22, amphiregulin, CXCL2, PTGS2, IL-1R1, IL-23R, G-CSF, and IL-22R.

19. The method of any one of paragraphs 1-18, wherein the one or more therapeutics comprise one or more antibiotics, antibodies, small molecules, kinase inhibitors, siRNAs, miRNAs, aptamers, natural or engineered autologous or allogenic immune cells, or combinations thereof.

20. The method of any one of paragraphs 1-19, wherein the one or more therapeutics comprises an antibiotic.

21. The method of paragraph 20, wherein the antibiotic is a restricted spectrum antibiotic.

22. The method of paragraph 20 or 21, wherein the antibiotic is in an inhalable or aerosolized form or formulation.

23. The method of any one of paragraphs 20-22, wherein the antibiotic is ampicillin, neomycin, metronidazole, vancomycin, azithromycin, clarithromycin, clindamycin, or erythromycin.

24. The method of any one of paragraphs 1-23, wherein the one or more therapeutics comprises an antibody.

25. The method of paragraph 24, wherein the antibody is canakinumab, secukinumab, ixekizumab, brodalumab, risankizumab, guselkumab, or tildrakizumab.

26. The method of any one of paragraphs 1-25, wherein the lung cancer is lung adenocarcinoma.

27. The method of any one of paragraphs 1-26, wherein the administration of the therapeutics is by local administration.

28. The method of any one of paragraphs 1-27, wherein the one or more therapeutics further comprises one or more other targeted therapies and/or immune-checkpoint blockage agents.

29. The method of any one of paragraphs 1-28, wherein the administration of the therapeutics reduces cancer cell proliferation or viability and/or reduces tumor burden in the subject.

30. The method of any one of paragraphs 1-29, wherein the reduction in the local bacterial load, block or depletion of tumor-infiltrating immune cells, local inhibition of one or more cytokines or chemokines, or a combination thereof, reduces cancer cell proliferation or viability and/or reduces tumor burden in the subject.

The present invention will be further understood by reference to the following non-limiting examples.

EXAMPLES

Example 1: Commensal Bacteria Promote Tumor Initiation and Progression in a Mouse Model of Lung Adenocarcinoma Materials and Methods Autochthonous GEM Model of Human LUAD The genetically-engineered mouse (GEM) model of human LUAD has previously been described (DuPage, et al.). In this model, the mice harbor conditional alleles of $Kras^{LSL-G12D}$ and $p53^{flox/flox}$ (KP mice). Upon intratracheal infection with adenoviral vectors expressing the Cre-recombinase under the control of the Sftpc promoter, oncogenic KrasG12D is activated and the tumor suppressor p53 is deleted in lung epithelial cells to induce lung adenoma and adenocarcinoma.

Germ-free KP mice were housed in gnotobiotic isolators, which were sampled every 2 weeks and confirmed negative for bacterial and fungal contaminants by culture, fecal Gram stain, and PCR using universal 16S rRNA primers. Both male and female mice were used in all experimental groups in all mouse experiments. KP mice were infected with $2.5 \times 10^8$ plaque-forming units (pfu) of Sftpc-Cre expressing adenovirus (Viral Vector Core, University of Iowa) through intratracheal instillation between 8-12 weeks of age to initiate tumors, as previously described (DuPage, et al.). Mice were randomized before treatments.

For antibiotic treatment, mice were given a cocktail of ampicillin (1 g/L, American Bioanalytical), neomycin trisulfate (1 g/L, Sigma), metronidazole (1 g/L, Sigma) and vancomycin (500 mg/L, Goldbio) (4Abx) in drinking water at indicated time points.

All studies were performed under a Massachusetts Institute of Technology Committee on Animal Care-approved animal protocol, or an ICUC approved animal study protocol at NIAID, NIH (LSB-1E and LSB-4E). Mice were assessed for morbidity according to MIT Division of Comparative Medicine guidelines and were humanely euthanized when ill.

Histology and Immunohistochemistry (IHC)

Tumor-bearing lung lobes and a portion of the spleen were fixed in 4% paraformaldehyde overnight and embedded in paraffin. Hematoxylin and eosin stain (H&E stain) was performed with a standard method (KI Histology Facility). IHC staining of Ki67 (Cell Signaling, 12202) was performed on 5 µm unstained sections after antigen retrieval with citrate buffer. Digitally scanned images of H&E or Ki67-stained slides were created with the Aperio ScanScope AT2 at 20× magnification and analyzed with the Aperio's WebScope software. For tumor burden quantification, tumor regions were outlined and the percentage of tumor area relative to total lung area was calculated for each mouse. For Ki67 index, tumor cells were classified based on the intensity of the nuclear Ki67 staining from 0 to 3+ by using a built-in Nuclear algorithm in the Webscope, and the percentage of nuclei with intense nuclear staining (3+) in total nuclei was calculated. All tumor burden/grading and IHC analyses were done in a blinded fashion, and at least five mice per groups were included in the analyses.

Statistical Analysis

GraphPad Prism 7 was used for statistical analyses with the histology/IHC/16S quantification and flow cytometry data. P-values from unpaired two-tailed student's t-tests were used for comparisons between two groups and one-way ANOVA with Bonferroni's post hoc test was used for multiple comparisons. For tumor burden and bacterial load correlation analysis, linear regression was performed with GraphPad Prism 7.

Results

Figure 1E:
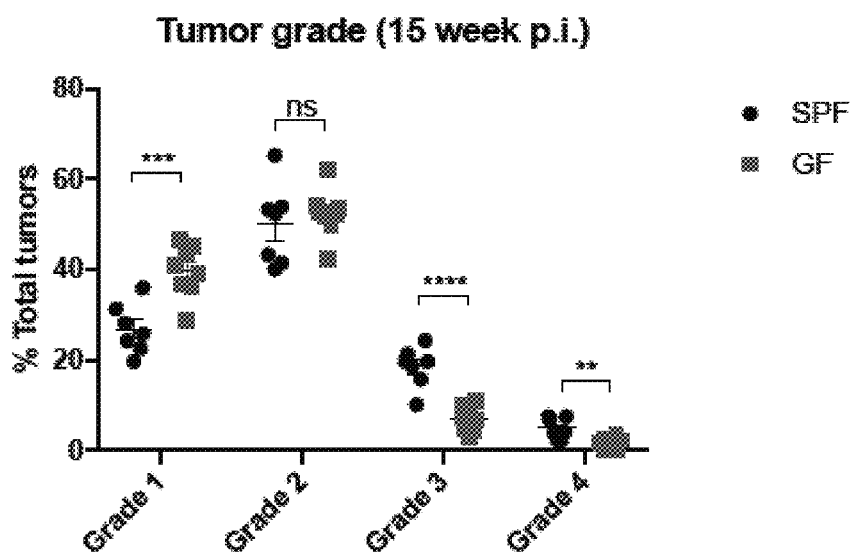
FIG. 1E is a graph showing comparison of tumor grades observed in KP mice under GF and SPF conditions at 15 weeks post infection.
Figure 1F:
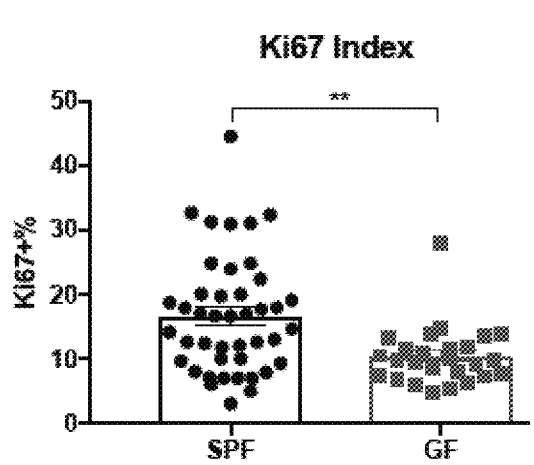
FIG. 1F is a graph showing comparison of tumor cell proliferation as assessed through the Ki67 index in KP mice under GF and SPF conditions. Approximately 50 tumors from 4-6 mice/group were analyzed.

To evaluate the functional importance of commensal bacteria in the initiation and progression of tumors in this mouse LUAD model, tumor development was compared between germ-free (GF) KP mice and their counterparts maintained under specific-pathogen-free (SPF) conditions. GF mice were significantly protected against lung tumorigenesis induced by Kras mutation and p53 deletion. Compared with age-matched SPF controls, GF KP mice exhibited substantially delayed tumor growth, with diminished tumor burden and decreased tumor numbers at both 8 weeks and 15 weeks post tumor initiation (FIGS. 1A-1D), and lower percentages of aggressive, high-grade lesions (FIG. 1E). At the cellular level, GF mice displayed reduced tumor cell proliferation as demonstrated by immunohistochemistry (IHC) analysis of Ki67 staining (FIG. 1F).

Figure 1G:
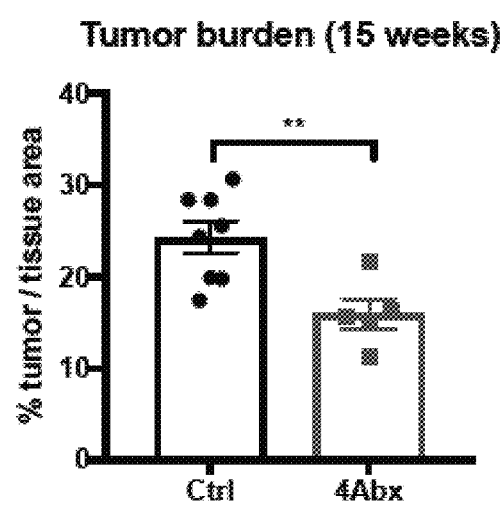
FIGS. 1G-1H are graphs showing tumor burden (FIG. 1G) and tumor grade (FIG. 1H) at 15 weeks post infection in SPF KP mice treated with combined antibiotics (4Abx) in drinking water. Results are expressed as the mean±SEM. n.s.=not significant,  $p<0.01$, * $p<0.001$, **** $p<0.0001$ by Student's t test. For each experiment, n=5-12 mice/group; data represent 3 independent experiments.
Figure 1H:
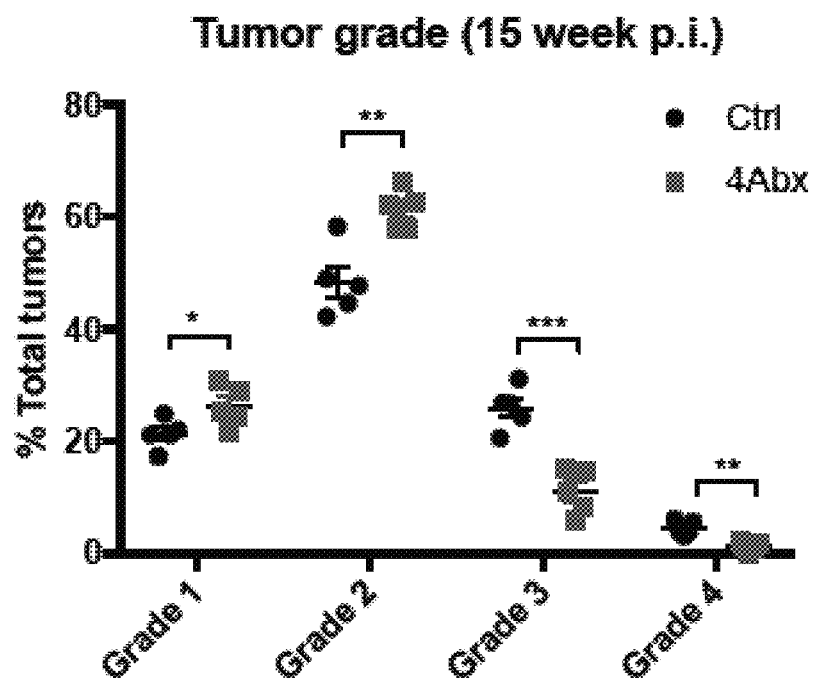

In this autochthonous KP model, mice develop atypical adenomatous hyperplasia (AAH) as early as 2-3 weeks post infection; the hyperplastic lesions then progress from small to large adenomas around 6-8 weeks, which further advance to adenocarcinomas. To determine the effects of microbiota on different stages of lung tumor progression, SPF KP mice were treated with an antibiotic cocktail (4Abx) of ampicillin (1 g/L), neomycin (1 g/L), metronidazole (1 g/L) and vancomycin (500 mg/L) in their drinking water at 6.5 weeks post infection. The combined antibiotic treatment robustly suppressed tumor growth in both early and advanced stages, resulting in significant reduction of high-grade tumors (FIGS. 1G-1H). Notably, antibiotic treatment did not affect the proliferation of tumor cells in vitro, arguing against the possibility of direct cytotoxic effects of these antibiotics. Together with the findings in GF KP mice, these results demonstrate that the commensal bacteria play a profound role in promoting tumor initiation and progression in the autochthonous GEM model of lung adenocarcinoma.

Example 2: Lung Tumor Development is Associated with Altered Local Microbiota and Increased Pro-Inflammatory Cytokine Expression Materials and Methods
Mouse Studies CD45.1 mice were purchased from Jackson Laboratory (Bar Harbor, Me.) and crossed to KP mice to generate KP-CD45.1 mice. For bone marrow chimera experiments, KP mice on the CD45.1 background were irradiated with a Gammacell-40 Irradiator (5.5 Gy×2, 3.5 hours apart), and then transplanted with bone marrow collected from wild type or Myd88 knockout donors (Jackson Laboratory) on the CD45.2 background. Seven weeks post bone marrow reconstitution, mice were infected with $2.5 \times 10^8$ pfu of Sftpc-Cre expressing adenovirus for tumor initiation.

Tumor burden quantification was performed as described in Example 1.

For antibiotic treatment, mice were given metronidazole (1 g/L, Sigma) alone in drinking water at indicated time points.

Cytokine Expression Analysis

Total RNA was isolated from lung tissues or FACS-purified cells using the RNeasy Plus Mini Kit (Qiagen) according to the manufacturer's instructions. cDNA was synthesized from RNA with the Superscript III Reverse Transcription Kit (Thermo Fisher). For real-time qPCR analysis, Il-1β and Il-23 expression were analyzed in triplicates and normalized to β-actin or Hprt with Taqman probes (Thermo Fisher) on a LightCycler 480 (Roche).

Lung and Fecal Microbiome Analysis

Bronchoalveolar lavage fluid (BALF) was collected with sterile PBS and centrifuged at 16,000 g for 10 minutes to pellet down bacterial cells. Fecal pellets were collected from the colon at the time of tissue harvest. BALF and fecal samples were processed for DNA isolation using a previously established protocol (Palm, et al., *Cell.* 158(5):1000-1010 (2014); Turnbaugh, et al., *Nature.* 457(7228):480-4 (2009)). For quantification of total bacterial burden, qPCR was performed with universal 16S primers targeting the V1-2 region (27F: AGAGTTTGATCMTGGCTCAG, 338R: TGCTGCCTCCCGTAGGAGT) and the Kapa SYBR Fast 2× master mix (Kapa Biosystems). *E. coli* genomic DNA was used as a standard, with samples at 1, 0.1, 0.01, and 0.001 ng per reaction used to create a standard curve. For 16S based sequencing, two rounds of PCR were utilized to prepare sequencing libraries (Caporaso, et al., *Proc. Natl. Acad. Sci. USA.*, 108 Suppl 1:4516-22 (2011); Preheim, et al., *Appl. Environ. Microbiol.*, 79(21):6593-603 (2013)). The first PCR amplified the V1-2 region of the 16S rRNA gene with 27F/338R, and added adapters at each end, followed by the second PCR adding full sequencing adapters and barcodes. Agencourt AMPure XP beads (Beckman Coulter) were used to purify the PCR products following the manufacturer's protocol and Kapa HiFi HotStart 2× Ready-Mix (Kapa Biosystems) was used for PCR reaction. The final PCR products were quantified using the Qubit DNA assay (Thermo Fisher Scientific), and all samples were normalized and pooled at equal mass for the final sequencing pool. Samples were sequenced on the Illumina MiSeq with 2×250 bp paired-end reads.

16S Sequencing Analysis 16S sequencing reads were processed using the QIIME analysis pipeline. OTUs were clustered at 97% identity using QIIME pick_open_reference_otus.py with the Greengenes 13.8 reference database (Caporaso et al., 2010). OTUs that did not appear in at least 3 samples and have at least 50 sequence counts were removed. On average, BAL samples had 50,000 sequencing reads and fecal pellet (FP) samples had 10,000 sequencing reads. A minimum threshold of 500 reads was used to retain samples after filtering. For alpha diversity, the Shannon index of the 97% identity OTUs was calculated using alph_diversity.py, with samples rarefied to 1000 reads. Beta diversity measurements were calculated using beta_diversity.py to determine the Bray-Curtis and weighted UniFrac metrics. PCoA plots were made using make_2d_plots.py. To test for differences in the community composition between sample groups, Permutational Multivariate Analysis of Variance (PERMANOVA) based on the Bray-Curtis and weighted UniFrac distance matrices was performed using QIIME compare_categories.py.

Results

Figure 2A:
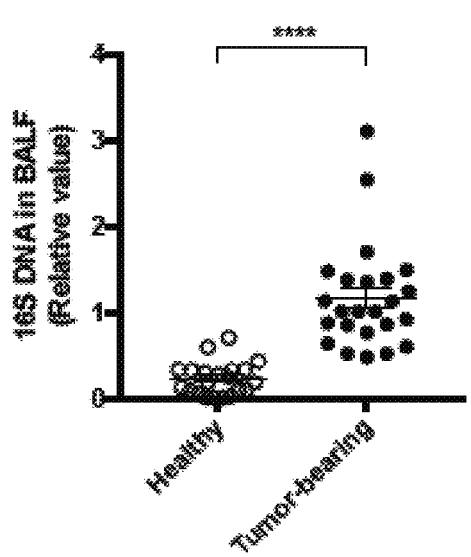
FIG. 2A is a graph showing the total bacterial burden in Bronchoalveolar lavage fluid (BALF) collected from tumor-bearing KP mice or healthy controls. Total bacterial was determined by 16S rDNA based qPCR analysis. Data were normalized to the corresponding median value of the tumor-bearing samples in each cohort.
Figure 2B:
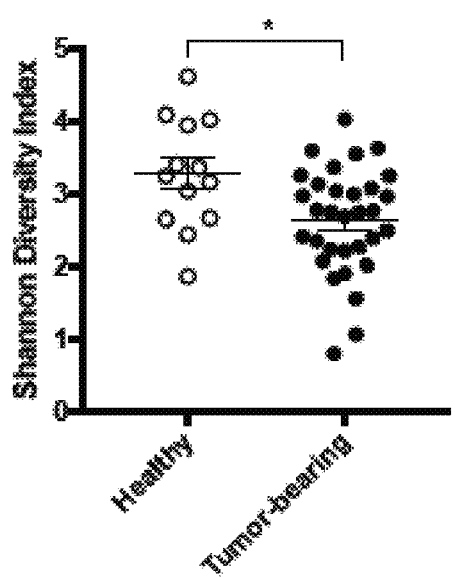
FIG. 2B is a graph showing the Shannon diversity index of the bacterial communities present in BALF. For FIGS. 2A-2B, data were pooled from 5 independent cohorts.
Figure 2C:
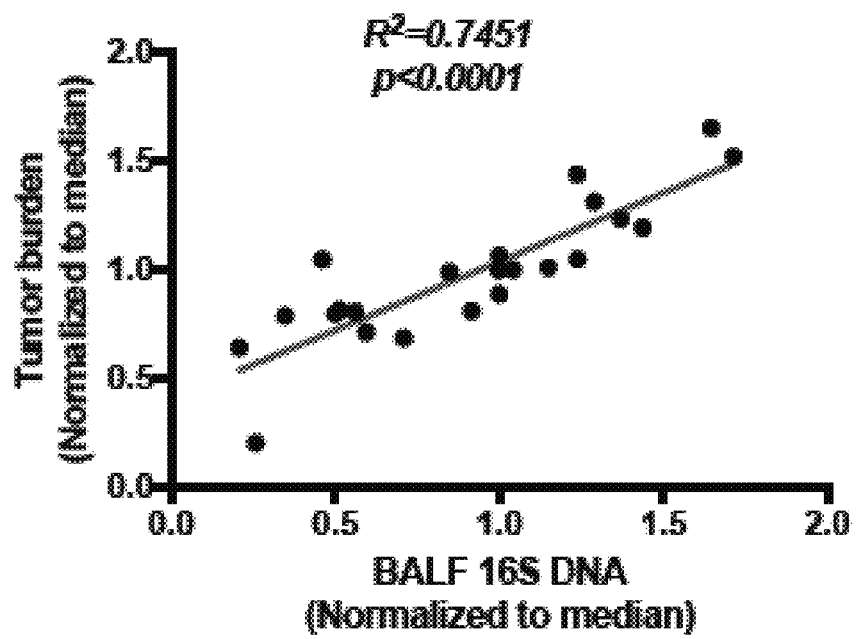
FIGS. 2C-2D are linear regression curves showing the correlation between tumor burden and bacterial load in BALF (FIG. 2C) or fecal pellet (FP.
Figure 2D:
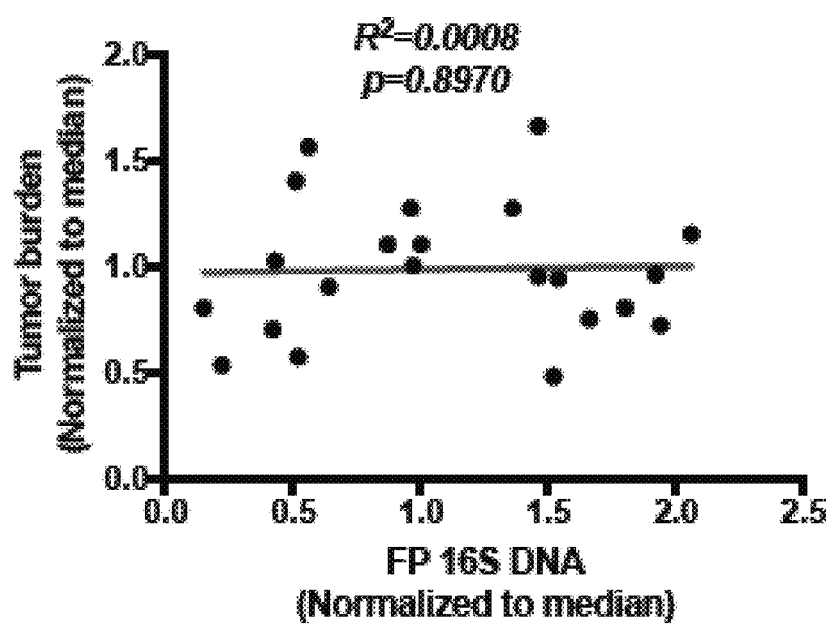
Figure 2E:
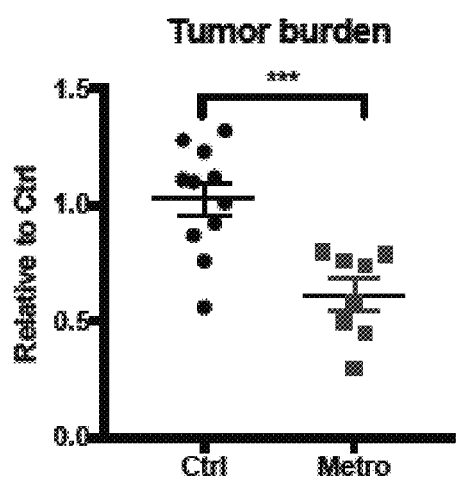
FIG. 2E is a graph showing quantification of tumor burden in metronidazole-treated KP mice and untreated controls. SPF KP mice were left untreated or treated with metronidazole alone in drinking water starting 5 weeks post tumor initiation.

To examine the relationship between the local microbiota and lung tumor development, 16S rDNA-based qPCR and sequencing was used to analyze the bacterial abundance and composition in bronchoalveolar lavage fluid (BALF). It was observed that the lungs from tumor-bearing KP mice harbored unique commensal bacterial communities as compared to the gut. In comparison to healthy (non-tumor bearing control) mice, the development of lung cancer was associated with a significant increase in the total bacterial burden as well as reduced bacterial diversity in the airway, as measured by the total amount of 16S DNA and the Shannon index of the bacterial community in the BALF (FIGS. 2A-2B). Of particular importance, the correlation between the microbiome and tumor development was local; in mice treated with antibiotics that partially eliminated the commensal bacteria, the local bacterial burden in the lung, but not the fecal bacterial load, was significantly correlated with the tumor burden (FIG. 2C-2D). In addition, treating mice with metronidazole alone effectively suppressed tumor growth in the lung without substantially reducing the overall bacterial abundance in the gut (FIG. 2E).

Figure 2F:
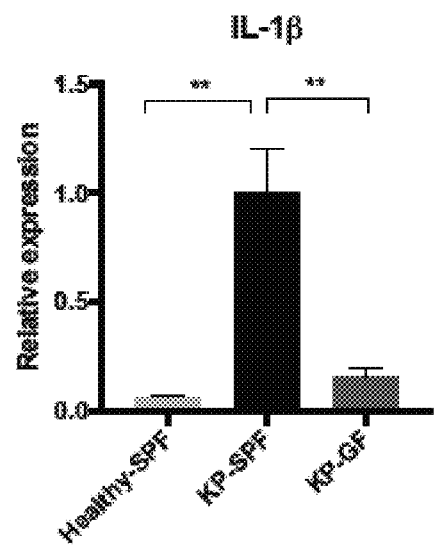
FIGS. 2F-2G are graphs showing RT-qPCR quantification of IL-1β (FIG. 2F) and IL-23 p19 (FIG. 2G) mRNA expression in the lung tissues from healthy SPF mice, tumor-bearing SPF mice and tumor-bearing GF mice.
Figure 2G:
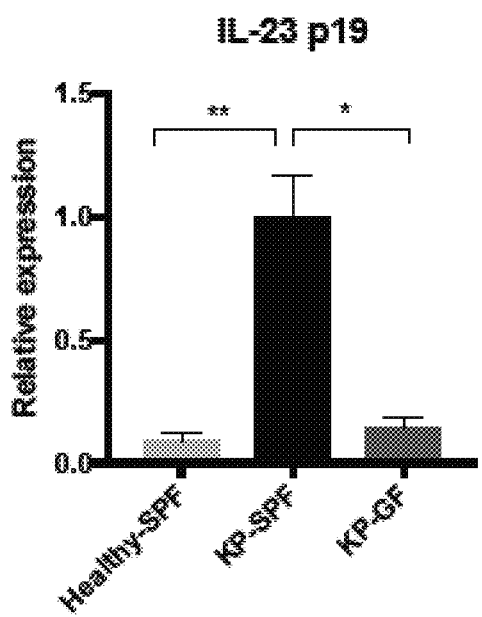
Figure 2H:
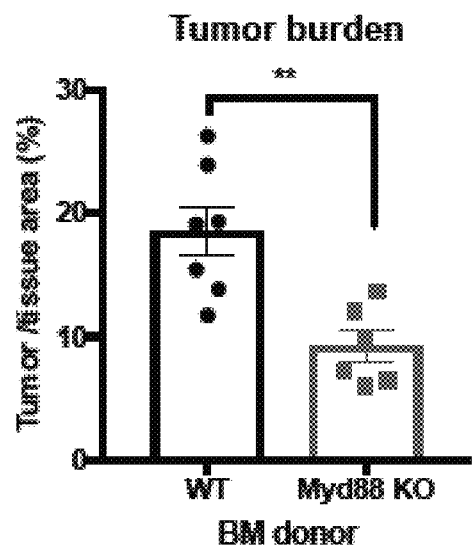
FIG. 2H is a graph showing quantification of tumor burden in KP mice on the CD45.1 background lethally irradiated and reconstituted with bone marrow from either wild-type (WT) or Myd88-deficient donors. Results are expressed as the mean±SEM.  $p<0.01$, * $p<0.001$, **** $p<0.0001$ by Student's t test. For each experiment, n=6-7 mice/group; data represent 3 independent experiments.

In comparison to healthy lungs, a significant increase in IL-1β and IL-23 p19 gene expression was associated with the increased local bacterial burden in the tumor-bearing lung tissues, and this increased cytokine expression was abrogated in GF mice (FIGS. 2F-2G). To examine the role of toll-like receptor (TLR) signaling in this response, KP-CD45.1 mice were reconstituted with bone marrow derived from Myd88 knockout donors. Hematopoietic deficiency of Myd88, an essential adaptor molecule downstream of multiple TLRs, inhibited the production of IL-1β and IL-23 from alveolar macrophages and neutrophils, resulting in significantly reduced tumor growth (FIG. 2H). These results indicate that bacterial products derived from airway microbiota may induce a pro-inflammatory response by activating the TLRs expressed on myeloid cells in the lung.

Example 3: Lung Adenocarcinoma is Associated with Microbiota-Induced Expansion of IL-17 Producing γδ T Cells Materials and Methods Flow Cytometry and FACS Sorting Mice were injected retro-orbitally with a PE-CF594 conjugated anti-CD45 antibody (30-F11, BD Bioscience) 2 minutes prior to euthanasia to label the immune cells in the circulation. Lungs were collected, cut into small pieces, and digested with 125 U/mL collagenase IV (Worthington Biochemical) and 40 U/mL DNase I (Roche) for 30 minutes at 37° C. Dissociated lung tissue was then filtered with a 100 µm cell strainer. Spleen and lymph node samples were ground and passed through a 100 µm cell strainer. After blocking FcgRIII/II with an anti-CD16/CD32 mAb (eBioscience), single cell suspensions were stained with the following antibodies: CD45.2 (104), CD45.1 (A20), Ly6G (1A8), CD11b (M1/70), TCRβ (H57-597), TCRγδ (GL3 or UC7-13D5), CD3 (17A2), CD4 (RM4-5), CD8 (53-6.7), Vγ1 (Vg1.1, 2.11), Vγ4 (Vγ2, UC3-10A6), IFN-γ (XMG1.2), IL-17A (TC11-18H10.1), TNF-α (MP6-XT22), IL-17F (ebio18F10), CD44 (IM7), CD27 (LG.3A10), CD69 (H1.2F3), PD-1 (29F. 1A12), PD-L1 (10F.9G2), T-bet (eBio4B10), RORγt (B2D), PLZF (Mags.21F7) and Ki67 (B56) purchased from eBioscience, BD or Biolegend. Biotinylated anti-amphiregulin antibody was purchased from R&D Systems. For intracellular cytokine staining, cells were pre-incubated with the Cell Stimulation Cocktail and the Protein Transport Inhibitor Cocktail (both from eBioscience) for 4 hours at 37° C. before surface staining. Transcription factor staining was performed using the Foxp3 Fixation/Permeabilization Solution Kit (eBioscience). Flow cytometry was performed on the LSR II or LSRFortessa (BD), and data were analyzed by the FlowJo software (Treestar). FACS sorting was performed on a FACSAria III (BD).

ELISA Analysis

IL-17 levels in serum or bronchoalveolar lavage fluid were measured using a mouse IL-17A ELISA kit (eBioscience) according to the manufacturer's instructions.

Immunofluorescence and Confocal Imaging

Lung tissues were perfused and then incubated in a fixation and permeabilization solution (BD Bioscience, 554722) overnight followed by dehydration in 30% sucrose before embedding in OCT compound (Sakura Finetek). 18-µm sections were cut on a CM3050S cryostat (Leica) and adhered to Superfrost Plus slides (VWR). Frozen sections were permeabilized and blocked in PBS containing 0.3% Triton X-100 (Sigma-Aldrich) and Fc-blocker (CD16/CD32 Monoclonal Antibody, eBioscience) followed by staining with antibodies diluted in the blocking buffer. The following antibodies were used for staining: anti-CD3 (17A2; Biolegend), anti-CD4 (GK 1.5, Biolegend), anti-CD8 (53-6.7, BD), anti-RORγt (Q31-378, BD) and anti-TCRγδ (GL3, Biolegend). After staining, slides were mounted with Fluormount G (Southern Biotech), and examined on a Leica TCS SP8 confocal microscope. Images were analyzed with Imaris software (Bitplane).

Results

Figure 3A:
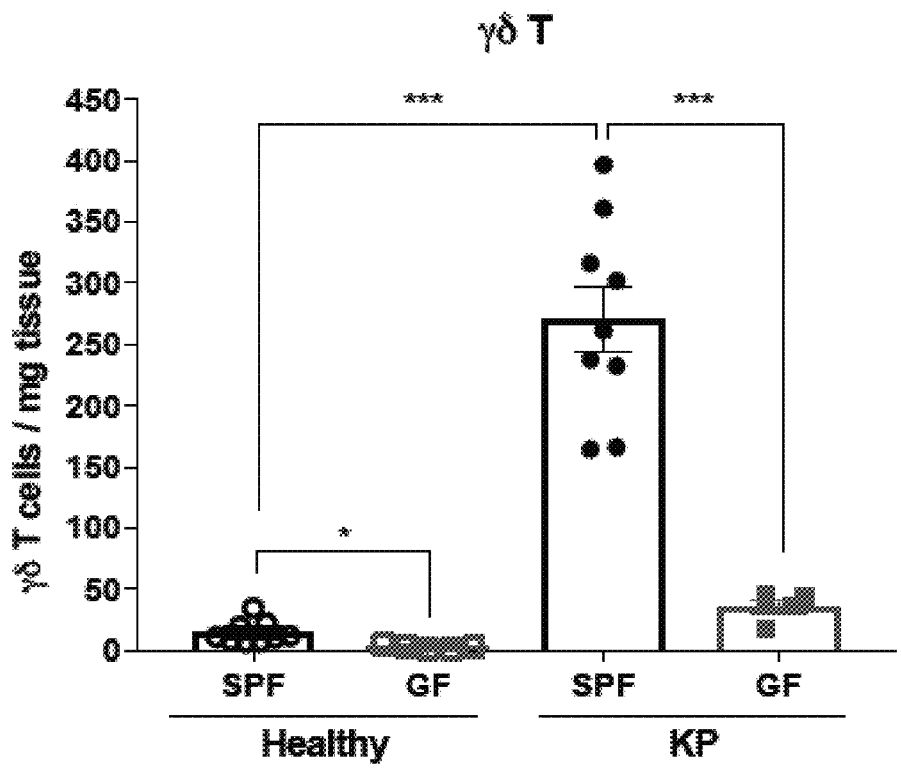
FIG. 3A is a graph showing flow cytometry based quantification of γδ T cells in the lung tissue from healthy or tumor-bearing SPF and GF mice.

To understand the cellular mechanism(s) of microbiota-mediated inflammation and tumor promotion linked to the presence of these pro-inflammatory cytokines in greater detail, the immune cells in tumor-bearing lungs from GF mice in comparison to SPF mice were analyzed by flow cytometry. Because the lung tissue is highly vascularized, mice were injected intravenously with phycoerythrin (PE)-labeled anti-CD45 antibodies just prior to euthanasia. This procedure labeled all hematopoietic cells in the circulation but not those localized inside the tissue (Anderson, et al., *J. Immunol.*, 189(6):2702-6 (2012); Anderson, et al., *Nat. Protoc.*, 9(1):209-222 (2014)). Using this approach, it was observed that γδ T cells only accounted for a minor fraction (~3-5%) of total CD3+ lymphocytes in the circulation or in peripheral lymphoid tissues (the spleen and the draining mediastinal lymph node). In contrast, γδ T cells were highly enriched in the tumor-bearing lung tissue of SPF mice (approximately 20% of total CD3+ lymphocytes). Importantly, the dramatic increase in γδ T cell abundance associated with lung adenocarcinoma in SPF mice was completely abrogated in the GF mice (FIG. 3A), suggesting that the commensal microbiota are critical for driving tumor-associated γδ T expansion.

Figure 3B:
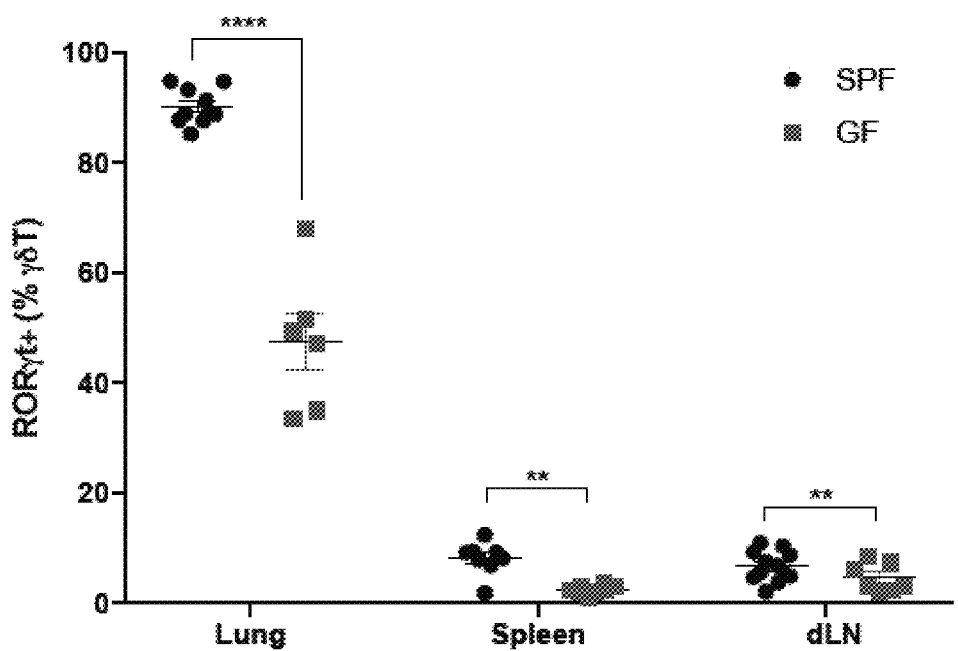
FIGS. 3B-3C are graphs comparing the frequencies of RORγt+ (FIG. 3B) or IL-17A+ (FIG. 3C)γδ T cells from the tumor-bearing lung, spleen, and draining lymph node (dLN) between SPF and GF mice.
Figure 3C:
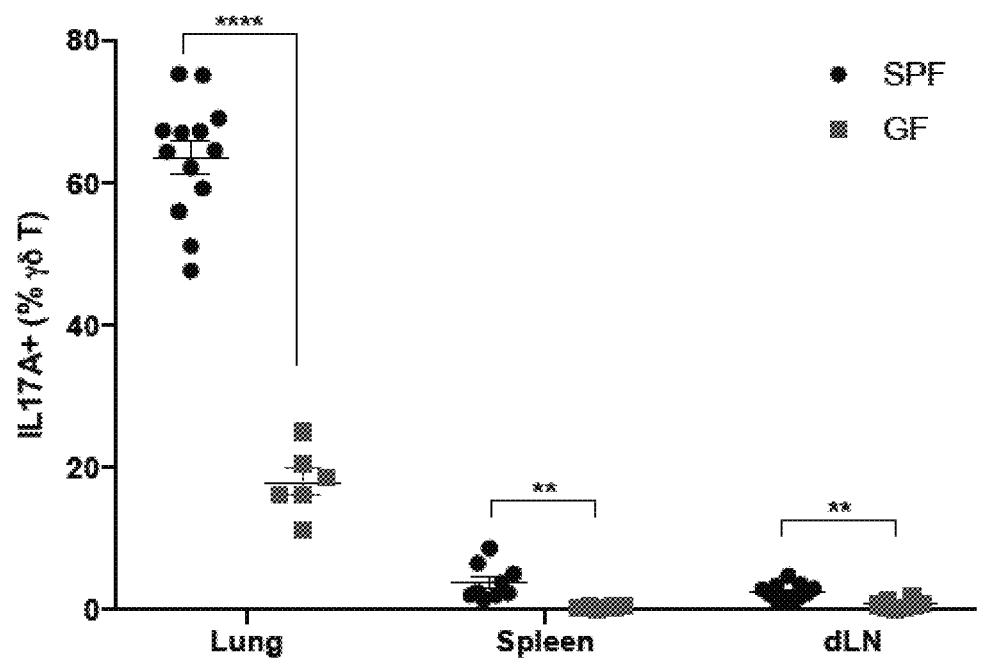

Among the γδ T cells that accumulated in the tumor-bearing lungs from SPF mice, ~90% expressed the transcriptional factor RORγt and up to 75% produced the pro-inflammatory cytokine IL-17A (defining these T cells as γδ T17 cells) (FIGS. 3B-3C). In comparison, only around 5% of the total γδ T cells in the spleen or draining lymph node (dLN) were IL-17 producers (FIG. 3C). In addition to the significant reduction in γδ T cell number in the tumor-bearing lungs, GF mice also exhibited dramatically decreased RORγt expression and IL-17 production in γδ T cells (FIGS. 3B-3C). These results imply that commensal microbiota not only impact the abundance of γδ T cells, but also play a critical role in determining their functionality. To examine the topographic distribution of these γδ T cells with respect to the developing tumors, multi-parameter confocal immunofluorescence microscopy was used. This analysis revealed infiltration of tumor lesions by γδ T17 cells in the SPF lungs that was absent in GF lungs.

Figure 3D:
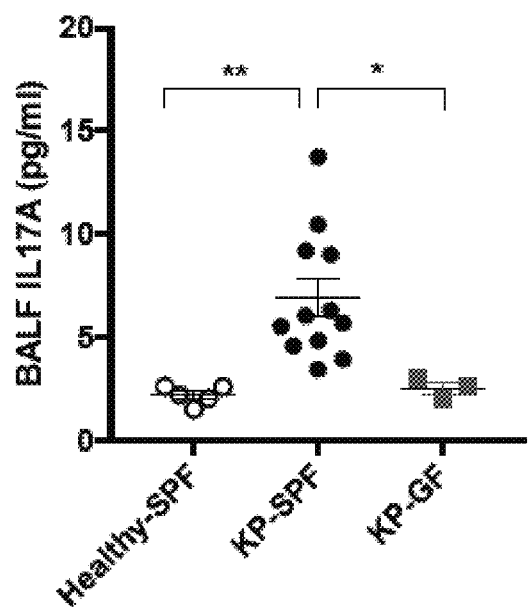
FIGS. 3D-3E are graphs showing IL-17A levels in BALF (FIG. 3D) and serum (FIG. 3E) samples collected from healthy SPF mice, tumor-bearing SPF mice and tumor-bearing GF mice as measured by ELISA. Results are expressed as the mean±SEM. *$p<0.05$,  $p<0.01$, * $p<0.001$, **** $p<0.0001$ by Student's t test. For each experiment, n=6-12 mice/group; data represent at least 4 independent experiments.
Figure 3E:
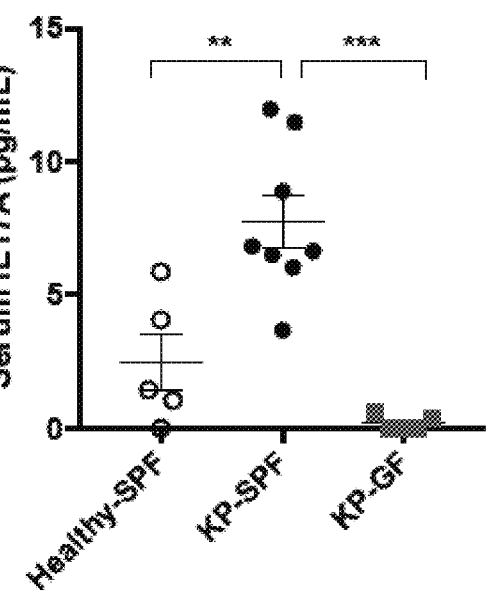

It is noteworthy that γδ T cells are a major source of IL-17 in the tumor-bearing lungs from SPF mice in this autochthonous GEM model of lung adenocarcinoma. They accounted for more than 60% of RORγt+ or IL-17+ lymphocytes whereas the other source of IL-17 was conventional CD4 T cells (i.e. Th17 cells). While no substantial difference in the Th17 compartment was observed between SPF and GF mice, IL-17A protein levels in the BALF and serum were significantly diminished in GF mice (FIGS. 3D-3E). Collectively, these data demonstrate that γδ T cells are the predominant IL-17 producing cells that accumulate in the lung in response to tumor development in a microbiota-dependent manner.

Example 4: Commensal Microbiota Induce Proliferation and Activation of Tissue-Resident Vγ6+Vδ1+ T Cells Materials and Methods Flow Cytometry and FACS Sorting Flow cytometry and FACS was performed as described above in Example 3. Briefly, for staining of the Vγ6Vδ1+ TCR, cells were labeled first with the anti-TCRγδ mAb (GL3), and then incubated with the supernatant from the 17D1 hybridoma (kindly provided by Dr. Robert Tigelaar and Julia Lewis, Yale University) followed by staining with the goat-anti-rat IgM (Jackson Immunoresearch Laboratories) secondary antibody as previously described (Roark, et al., *J. Leukoc. Biol.*, 75(1):68-75 (2004)). Flow cytometric analysis of Ki67 expression was used to assess proliferation of γδ T17 cells. Flow cytometry was performed on the LSR II or LSRFortessa (BD), and data were analyzed by the FlowJo software (Treestar). FACS sorting was performed on a FACSAria III (BD).

ELISA Analysis

IL-17 levels were measured using a mouse IL-17A ELISA kit (eBioscience) according to the manufacturer's instructions.

Mouse Studies

For in vivo stimulation of γδ T cells in the lung, recombinant mouse IL-1β (R&D Systems, 100 ng/mouse) plus IL-23 (R&D Systems, 100 ng/mouse), or LPS (Lipopolysaccharide from *E. coli* O111:B4, Invivogen, 2 μg/mouse) plus PGN (Peptidoglycan from *S. aureus*, Invivogen, 5 μg/mouse) were administered intratracheally to wild-type C57BL/6J mice.

All studies were performed under a Massachusetts Institute of Technology Committee on Animal Care-approved animal protocol, or an ICUC approved animal study protocol at NIAID, NIH (LSB-1E and LSB-4E). Mice were assessed for morbidity according to MIT Division of Comparative Medicine guidelines and were humanely euthanized when ill.

Results

One of the key features distinguishing γδ T cells from αβ T cells is their limited TCR diversity, with preferential usage of specific TCR Vγ chains depending on their effector function and tissue localization (Vantourout and Hayday, *Nat. Rev Immunol.*, 13:88-100 (2013)). Vγ1+, Vγ4+ and Vγ6+γδ T cells have all been reported to exist in the lung, and their relative abundance seems to be context dependent during different types of infection or inflammatory conditions (Cheng and Hu, *Immunology.*, 151:375-384 (2017); Papotto, et al., *Nat. Immunol.*, 18:604-611 (2017)). It was observed that the expanded γδ T17 population in KP lungs consisted primarily of Vγ6+Vδ1+ T cells. These cells accounted for an average of 80% of total γδ T cells, and more than 90% of the γδ T17 population. In contrast, only a small fraction of γδ T17 cells were Vγ4+, whereas Vγ1+γδ T cells made up fewer than 5% of total γδ T cells and most of them did not express RORγt. It was observed that the IL17-producing Vγ6+Vδ1+ T cells that expanded in tumor-bearing lungs were highly resistant to radiation and reconstitution. Twenty weeks after transplantation of lethally irradiated KP-CD45.1 mice with bone marrow from CD45.2 donors, γδ T cells were readily detected in tumor-bearing lungs. However, despite the robust reconstitution of Tbet+γδ T cells or the Vγ4+γδ T cell compartment by the donor bone marrow, RORγt+γδ T cells were largely of the recipient origin in these chimeras and donor-derived Vγ6+Vδ1+ T cells were virtually absent.

Figure 4A:
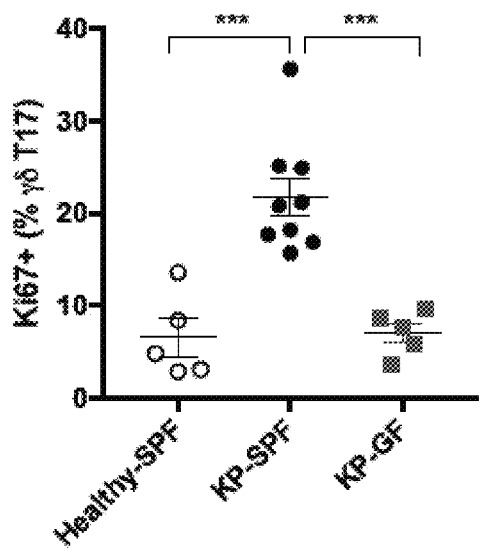
FIG. 4A is a graph showing proliferation of γδ T17 cells in the lungs from healthy SPF mice, tumor-bearing SPF mice and tumor-bearing GF mice as assessed by flow cytometric analysis of Ki67 expression.
Figure 4B:
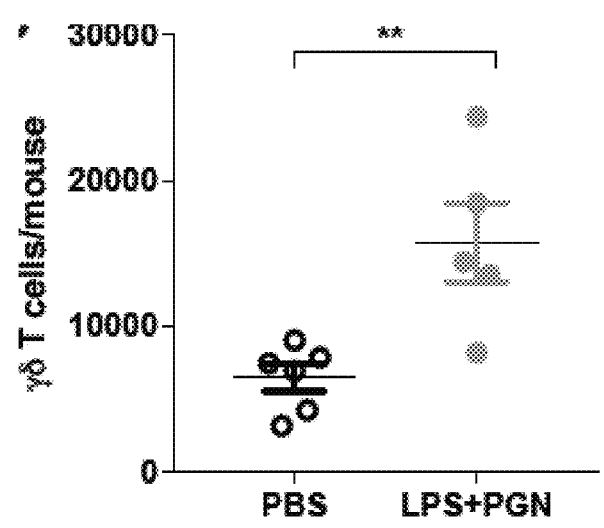
FIGS. 4B-4C are graphs showing the number (FIG. 4B) and IL-17 expression (FIG. 4C) of γδ T cells in mouse lungs analyzed 36 hours post local delivery of LPS and PGN.
Figure 4C:
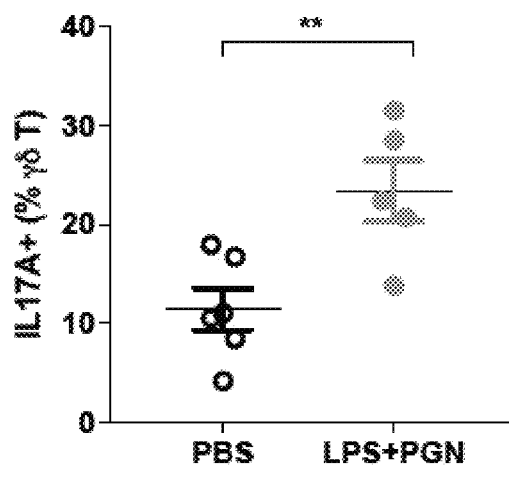
Figure 4D:
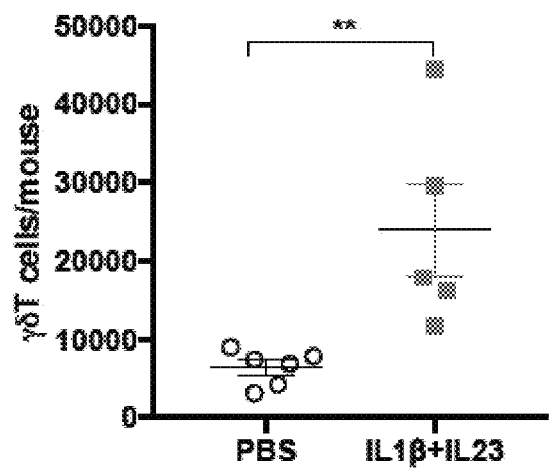

The lung-resident origin of these γδ T cells strongly indicated that tumor-associated γδ T expansion was largely due to local proliferation rather than recruitment from the circulation. In support of this hypothesis, increased proliferation of γδ T cells, particularly those expressing IL-17, was observed in tumor-bearing lungs compared to healthy lungs, which was largely abrogated in the GF mice (FIG. 4A). In comparison, no apparent changes in the proliferation of RORγt-γδ T cells or Th17 cells were observed in GF mice, arguing against a global reduction in cell proliferation in GF animals. Moreover, associated with the increased bacterial load in the airway, IL-17 production from γδ T cells in the tumor-bearing lungs was substantially enhanced as compared to that from cells in healthy lungs. Reducing the commensal microbiota with 4Abx or metronidazole dramatically decreased the abundance of IL-17 producing γδ T cells in the tumor-bearing lung, resulting in lower IL-17A levels in the BALF or serum. Taken together, these data suggest that a tumor-associated increase in the local bacterial burden induces proliferation and activation of tissue-resident IL17-producing γδ T cells. Further supporting this model, local administration of TLR ligands (such as lipopolysaccharide, LPS and peptidoglycan, PGN) was able to trigger the expansion and IL-17 production of γδ T cells in the lung (FIGS. 4B-4C). In addition, direct stimulation of the lung γδ T17 cells via intratracheal delivery of IL-1β and IL-23, the pro-inflammatory mediators produced by myeloid cells upon microbial exposure, also potently induced their proliferation and activation (FIGS. 4D-4F).

Example 5: Commensal Microbiota are Important for the Differentiation and Activation of Tumor-Associated γδT Cells in the Lung Materials and Methods Flow Cytometry and FACS Sorting Flow cytometry and FACS was performed as described above in Example 3. Briefly, single cell suspensions from lung or spleen were stained with the following antibodies: CD44 (IM7), CD27 (LG.3A10), CD69 (H1.2F3), PD-1 (29F. 1A12), and PLZF (Mags.21F7) purchased from eBioscience, BD or Biolegend. For intracellular cytokine staining, cells were pre-incubated with the Cell Stimulation Cocktail and the Protein Transport Inhibitor Cocktail (both from eBioscience) for 4 hours at 37° C. before surface staining. Transcription factor staining was performed using the Foxp3 Fixation/Permeabilization Solution Kit (eBioscience).

Results

Figure 5B:
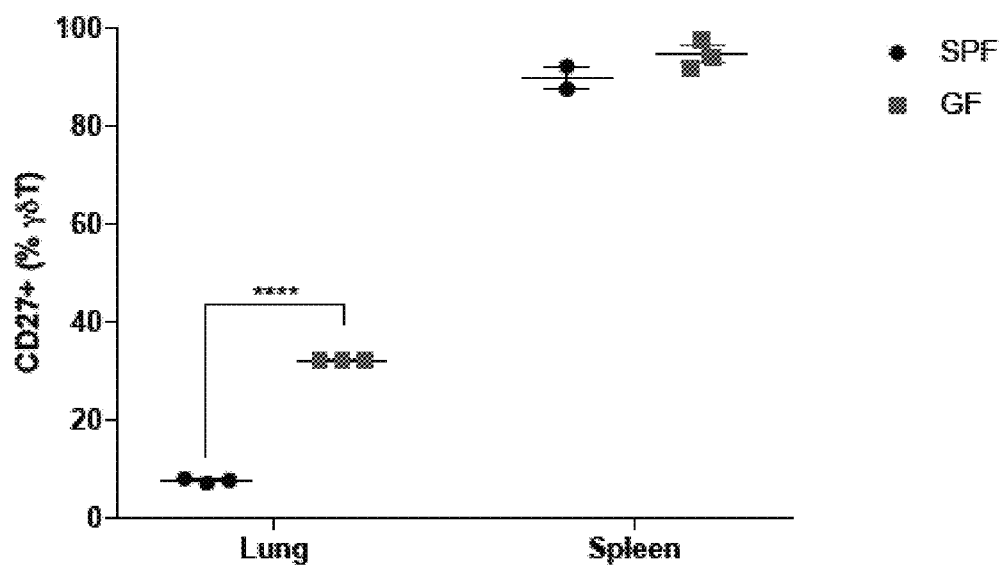
Figure 5C:
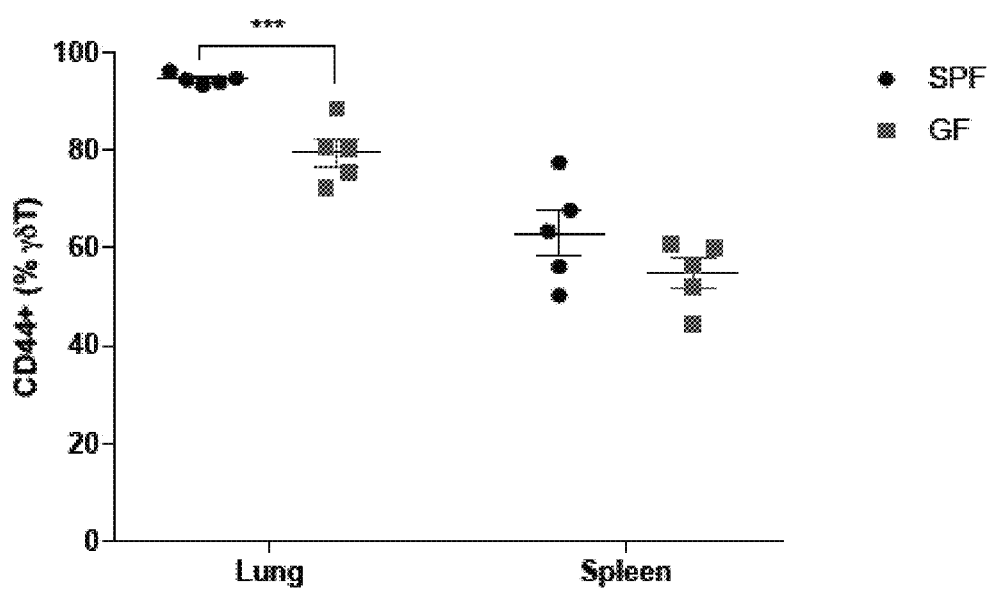
Figure 5D:
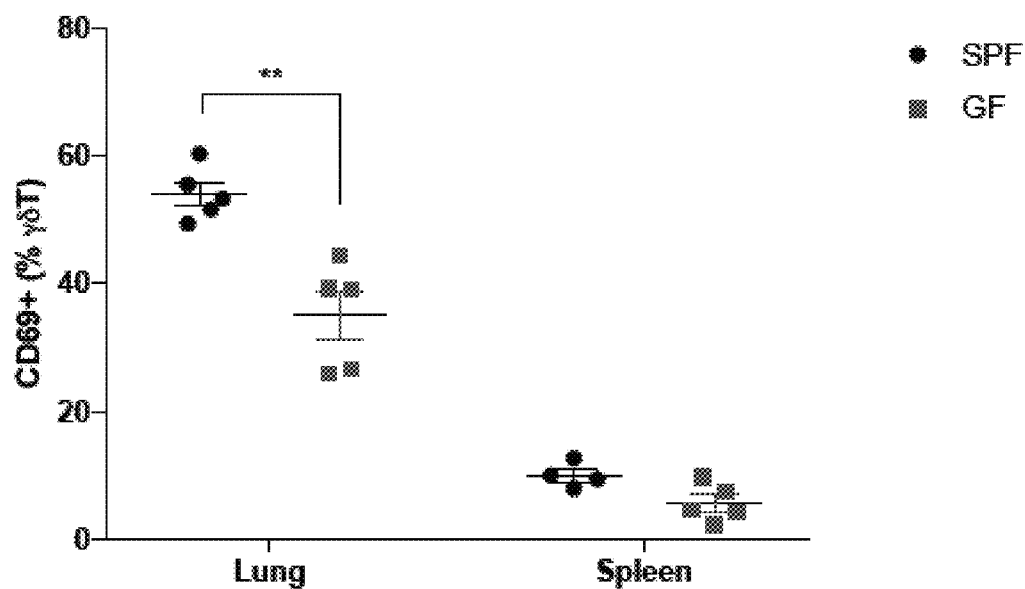
Figure 5E:
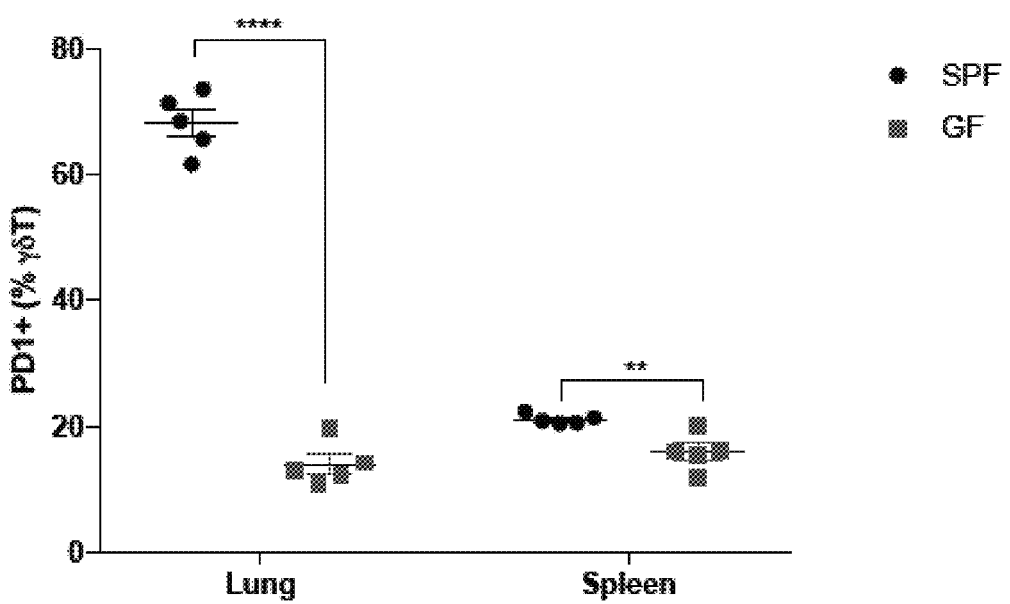

Upon further characterization, the immunophenotype of γδ T cells in the tumor-bearing lungs from SPF mice were found to exhibit minimal capacity for IFNγ or TNFα production coupled with low expression of the transcription factor Tbet. In contrast to splenic γδ T cells, γδ T cells in the tumor-bearing lungs were largely positive for promyelocytic leukemia zinc finger (PLZF) (FIG. 5A), which is a transcription factor essential for the development of tissue-resident IL17-producing Vγ6+γδ T cells. In addition, they displayed low surface expression of CD27 (FIG. 5B), which is critical for the differentiation of IFNγ-producing γδ T cells. Consistent with the fact that they were activated by the local microbiota, γδ T cells in the tumor-bearing SPF lungs also showed elevated surface expression of activation/maturity markers including CD44, CD69 and PD1 as compared to those in the spleen (FIGS. 5C-5E). However, γδ T cells from the tumor-bearing lungs of the GF mice displayed a different phenotype: they had higher expression of IFNγ, Tbet and CD27, but significantly lower expression of PLZF as well as CD44, CD69 and PD1 (FIGS. 5A-5E). These results indicate that commensal microbiota are critical for the differentiation and activation/maturation of tumor-associated γδ T cells in the lung.

Example 6: Microbiota-Induced γδ T Cells Promote Neutrophil Infiltration and Tumor Development Materials and Methods Neutrophil Quantification Flow cytometry and FACS was performed as described above in Example 3 to determine neutrophil abundance. Neutrophil infiltration was assessed by flow cytometry and IHC analysis. Briefly, samples were fixed in 4% paraformaldehyde overnight and embedded in paraffin. Hematoxylin and eosin stain (H&E stain) was performed with a standard method (KI Histology Facility). IHC staining of Ly6G (BD Pharmingen, 1A8) was performed on 5 μm unstained sections after antigen retrieval with proteinase-K (Sigma). Digitally scanned images of the stained slides were created with the Aperio ScanScope AT2 at 20× magnification and analyzed with the Aperio's WebScope software.

ELISA Analysis

IL-17A levels were measured using a mouse IL-17A ELISA kit (eBioscience) according to the manufacturer's instructions.

QPCR Analysis of Cytokine Expression

G-CSF and IL-1β mRNA expression in the lung tissue were measured by RT-qPCR. Briefly, total RNA was isolated from lung tissues or FACS-purified cells using the RNeasy Plus Mini Kit (Qiagen) according to the manufacturer's instructions. cDNA was synthesized from RNA with the Superscript III Reverse Transcription Kit (Thermo Fisher). For real-time qPCR analysis, Il-1β and Gcsf expression were analyzed in triplicates and normalized to β-actin or Hprt with Taqman probes (Thermo Fisher) on a LightCycler 480 (Roche).

Mouse Studies

For antibody-mediated depletion experiments, animals were treated every 2-3 days with i.p. injection of neutralizing monoclonal antibodies (200 μg/mouse) directed against γδ-TCR (UC7-13D5, BioXCell; or GL3, purified from the hybridoma generously provided by Dr. O'Brien, National Jewish Health, Denver) or IL-17A (17F3, BioXCell), and their isotype controls (BioXCell). All studies were performed under a Massachusetts Institute of Technology Committee on Animal Care-approved animal protocol, or an ICUC approved animal study protocol at NIAID, NIH (LSB-1E and LSB-4E). Mice were assessed for morbidity according to MIT Division of Comparative Medicine guidelines and were humanely euthanized when ill.

Tumor burden was determined as described in Example 1. Tumor cell proliferation was assessed by Ki67 index (50-60 tumors from 5 mice/group) as described in Example 1.

Results

Figure 6A:
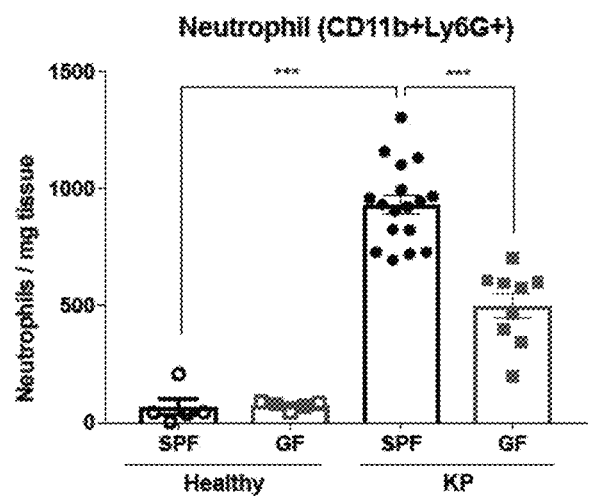
FIG. 6A is a graph showing the number of neutrophils in the lungs from SPF and GF mice as determined by flow cytometry.
Figure 6B:
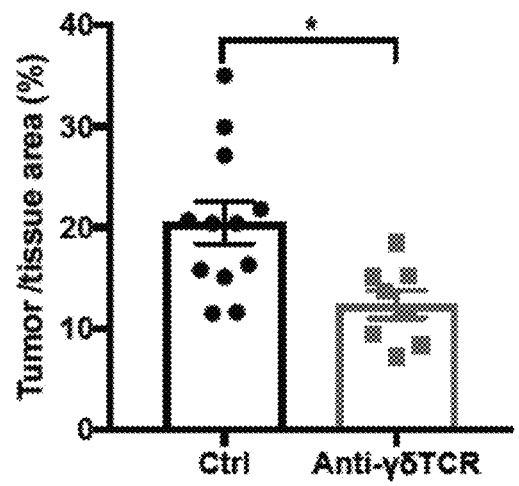
FIGS. 6B-6E are graphs showing tumor burden at 15 weeks post infection (FIG. 6B), serum IL-17A levels determined by ELISA (FIG. 6C), neutrophil abundance determined by flow cytometry (FIG. 6D), and tumor cell proliferation determined by Ki67 index (50-60 tumors from 5 mice/group.
Figure 6C:
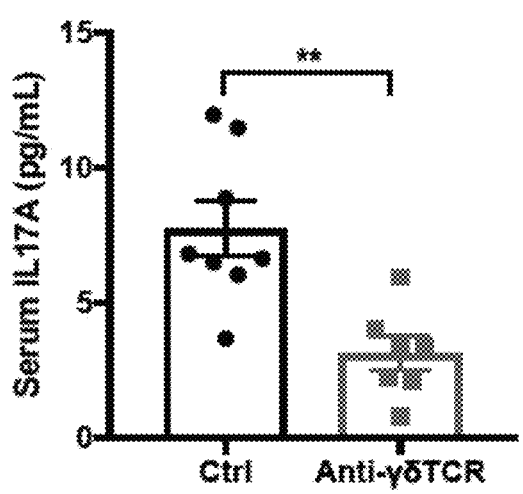
Figure 6D:
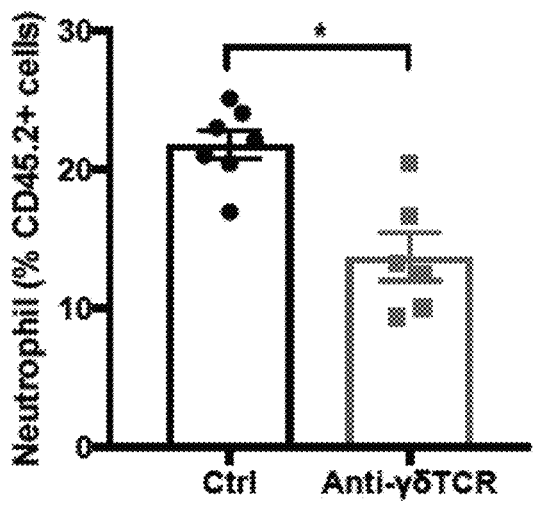
Figure 6E:
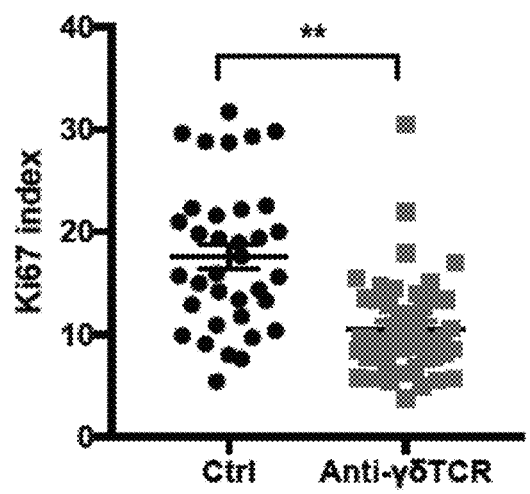
Figure 6F:
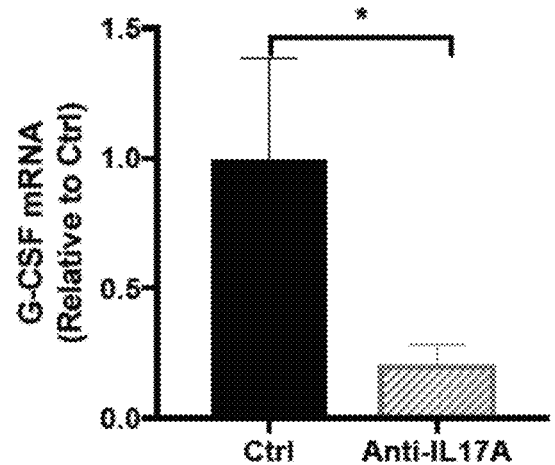
FIGS. 6F-6G are graphs showing RT-qPCR mRNA expression of G-CSF (FIG. 6F) and IL-1β (FIG. 6G) in the lung tissue of KP mice treated with a monoclonal antibody that neutralizes IL-17A.
Figure 6G:
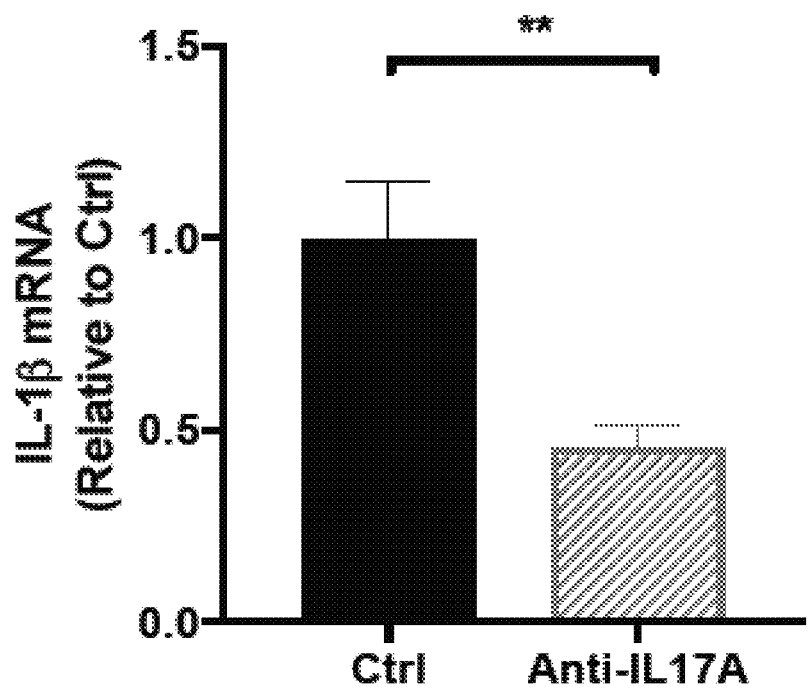
Figure 6H:
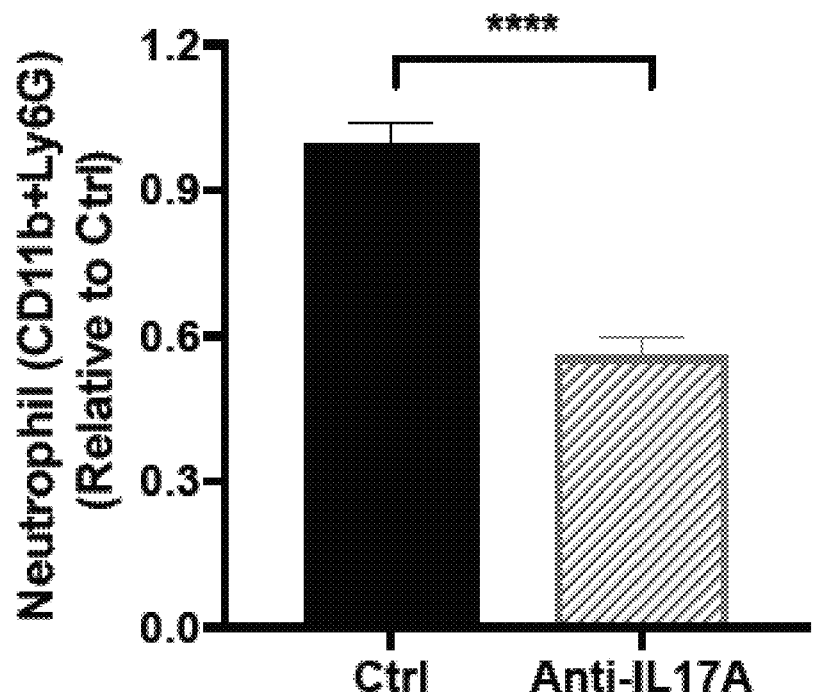
FIGS. 6H-6I are graphs showing neutrophil infiltration (FIG. 6H) as assessed by flow cytometry, and tumor burden at 13-15 weeks post infection (FIG. 6I) in KP mice treated with the IL-17A neutralizing antibody.
Figure 6I:
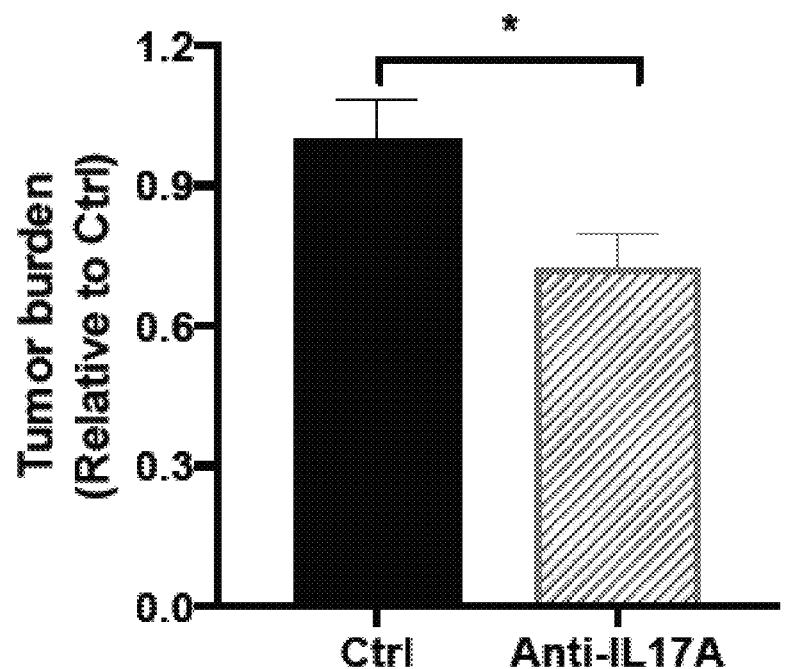

Lung-resident γδ T cells are thought to be critical for host immune defense against bacterial infections (Papotto, et al., 2017) but their role in tumor initiation and progression is not known. Therefore, the cellular and molecular mechanism(s) by which microbiota-induced γδ T cells promoted lung cancer development was next explored. Accompanying the expansion of γδ T cells, neutrophil infiltration was also dramatically increased in tumor-bearing lungs as compared to healthy lungs in SPF mice, and this response was suppressed in GF mice (FIG. 6A). While neutrophils are implicated in promoting tumorigenesis and cancer metastasis in various tumor models including lung cancer (Coffelt, et al., Nat. Rev. Cancer, 16:431-446 (2016); Houghton et al., Nat. Med., 16: 219-223 (2010)), the upstream signal inducing the expansion of neutrophils in the KP tumors has not been clearly identified. To assess the functional importance of γδ T cells in mediating the microbiota-dependent neutrophil expansion and tumor promotion, KP mice were treated with monoclonal antibodies against γδ T cells (UC7-13D5 or GL3) 4 weeks after tumor initiation and their effects on tumor development were evaluated. Both of these antibodies effectively blocked γδ T cells in the lung, and significantly inhibited the progression of lung adenocarcinoma. Mechanistically, depletion of γδ T cells substantially reduced the IL-17A level, resulting in decreased neutrophil infiltration and tumor cell proliferation (UC7-13D5: FIGS. 6B-6E).

The data clearly demonstrated microbiota-activated γδ T cells as a major cellular source of IL-17A in KP tumors. IL-17A has been implicated both in tumor-promoting inflammation and anti-tumor immunity, with contradictory roles being reported for IL-17A in different models of lung cancer (Akbay, et al., J. Thorac. Oncol., 12:1268-1279 (2017); Chang, et al., Proc. Natl. Acad. Sci. USA., 111:5664-5669 (2014); Cheng, et al., Cancer Res., 74:4030-4041 (2014)). Therefore, an IL-17A neutralizing antibody was used to evaluate the relevance of IL-17A in the context of the KP model. The results showed that IL-17A blockade led to drastically decreased G-CSF expression and neutrophil infiltration in the lung, as well as a significant reduction in tumor growth and IL-1β expression (FIGS. 6F-6I).

γδ T cells were previously shown to promote pancreatic oncogenesis by suppressing the anti-tumor CD4 and CD8 cell responses via the expression of immunomodulatory molecules such as PD-L1 (Daley, et al., Cell, 166:1485-1499 e1415 (2016)). Interestingly, no elevation of PD-L1 expression on tumor-infiltrating γδ T cells in the lung compared to those in the blood or lymph node in either SPF mice or GF mice was observed, and no significant difference was observed in the anti-tumor activities of the tumor-associated CD4 or CD8 cell compartments between SPF and GF mice. Moreover, γδ T cell depletion did not affect the proliferation or type 1 effector cytokine production of CD4 or CD8 cells. In summary, these findings indicate that microbiota-induced γδ T cells play a pivotal role in mediating neutrophil infiltration and tumor cell proliferation during the development of lung cancer, and IL-17A is a key effector molecule involved in this process. Blocking γδ T cell or IL-17 exhibited potent therapeutic efficacy in treating lung adenocarcinoma.

Example 7: γδ T Cells Associated with Lung Tumors Exhibit a Distinct Transcriptional Profile Materials and Methods Mouse Studies R26$^{LSL-cas9}$ mice were purchased from Jackson Laboratory (Bar Harbor, Me.) and crossed to KP mice to generate KP-R26$^{LSL-cas9}$ mice. Mice were infected with 30,000 transforming units of lentiviral vectors co-expressing Cre and specific sgRNAs through intratracheal instillation between 8-12 weeks of age to initiate tumors, as previously described (DuPage, et al.). Mice were randomized before treatments.

Tumor burden was determined as described in Example 1.

RNA-Seq Sample Preparation

γδ T cells were isolated from tumor bearing lungs or spleens of KP mice by FACS. Approximately 1000 cells/condition were sorted directly into TCL buffer (Qiagen), and the sequencing libraries were prepared using a modified Smartseq V2 protocol as previously described (Picelli, et al., Nat. Protoc., 9:171-181 (2014); Singer, et al., Cell, 171: 1221-1223 (2017)). A total of 9 spleen and 15 lung samples from three independent experiments were sequenced on the Illumina HiSeq 2000 platform.

RNA-Seq Analysis

Illumina HiSeq 2000 40-nt single-ended reads were mapped to the UCSC mm9 mouse genome build (genome.ucsc.edu) using RSEM (Li and Dewey, BMC Bioinformatics, 12:323 (2011)). Raw estimated expression counts were upper-quartile normalized to a count of 1000 (Bullard, et al., BMC Bioinformatics, 11:94 (2010)). Genes with an upper-quartile expression distribution value less than 20 in both conditions were considered lowly expressed and dropped from downstream analyses. The expression dataset was log (base 2) transformed to stabilize variance. KP-lung (n=15) and KP spleen (n=9) samples were jointly analyzed to derive a murine signature of lung γδ T gene expression. A high-resolution signature discovery approach (Independent Component Analysis, ICA) was employed to characterize changes in gene expression profiles as described previously (Li et al., *Genes Dev.*, 29:1850-1862 (2015); Romero, et al., *Nat. Med.*, 23:1362-1368 (2017)). Briefly, this unsupervised blind source separation technique was used on this discrete count-based expression dataset to elucidate statistically independent and biologically relevant signatures. ICA is a signal processing and multivariate data analysis technique in the category of unsupervised matrix factorization methods (Hyvarinen and Oja, *Neural Netw.*, 13:411-430 (2000)). The R implementation of the core JADE algorithm (Joint Approximate Diagonalization of Eigenmatrices) (Biton, et al., *Cell Rep.*, 9:1235-1245 (2014); Miettinen, et al., *J. Stat Softw.*, 76:1-31 (2017); Rutledge and Bouveresse, *Trac-Trend. Anal. Chem.*, 50:22-32 (2013)) was used along with custom R utilities. Statistical significance of biologically relevant signatures was assessed using the Mann-Whitney-Wilcoxon test (alpha=0.05). Signature genes with |z-score|>3 and |fold-change|>2 were used to generate a heatmap illustrating changes in gene expression, with the HeatPlus package in R. Gene set enrichment analyses (GSEA) were carried out using the signature scores per gene (z-scores) in pre-ranked mode with default settings (Subramanian, et al., *Proc. Natl. Acad. Sci. USA*, 102:15545-15550 (2005)). A volcano plot was used to illustrate the magnitude of fold-change for top-scoring (z-scores) genes in the signature. The expression levels of 8 biologically relevant top-scoring genes in the signature were illustrated using a pairwise dot-plot between lung and spleen samples. False discovery rate (FDR) values for differential expression status of these genes were calculated using a pairwise comparison in EBSeq (Leng, et al., *Bioinformatics*, 29:1035-1043 (2013)). All RNA-seq analyses were conducted in the R Statistical Programming language (http://www.r-project.org/).

Data Accessibility

The RNA-seq data for γδ T cells from tumor-bearing lungs or spleens of KP mice have been deposited in the GEO repository under the ID code GSE114340.

Clinical Data Analysis

IL-22 receptor (IL22RA1) expression levels were compared between normal and tumor tissue within the TCGA (cancergenome.nih.gov) Lung Adenocarcinoma (LUAD) cohort. Matched normal and tumor tissue IL22RA1 standardized expression levels were illustrated using an Empirical Cumulative Distribution Function plot (ECDF) and significance was assessed using a Kolmogorov-Smirnov test. Similarly, the set of normal samples was compared with the entire set of tumor samples (either with or lacking matched normal samples). For survival analysis, RNA-seq gene expression profiles of primary tumors and relevant clinical data of 515 lung adenocarcinoma (LUAD) patients were obtained from TCGA and survival analyses were conducted as described previously (Romero, et al., (2017); Tammela, et al., *Nature*, 545:355-359 (2017)). The murine KP-lung derived γδ T gene expression signature (|z|>3 genes) was translated to human symbols (homology information from MGI, informatics.jax.org) and was used to score individual TCGA tumor expression profiles using ssGSEA (Barbie, et al., *Nature*, 462:108-112 (2009)). Patients were stratified based on standardized ssGSEA scores and Kaplan-Meier survival analyses were conducted to compare high-scoring patients (top quartile) with low-scoring patients (bottom quartile) and significance was assessed using the log-rank test. For Kaplan-Meier survival analysis based on IL22RA1 expression, TCGA LUAD cohort patients were similarly stratified based on standardized expression values of IL22RA1 and the top 30% of patients were compared with the rest of the cohort. All survival analyses were conducted using the survival package in R.

In Vitro Cell Proliferation

Tumor cell lines were derived from primary lung tumors of KP mice, and maintained in DMEM medium (Gibco) supplemented with 10% FBS (Sigma). Cells were serum-starved for 24 hours (1% FBS) before treated with recombinant human amphiregulin (Sigma-Aldrich) or recombinant mouse IL-22 (R&D Systems) at the indicated dose, or left untreated as controls. The number of live cells was determined 72 hours post treatment by counting the Trypan Blue (Gibco) negative cells or through the CellTiter-Glo Luminescent Cell Viability Assay (Promega) according to the manufacturer's instructions.

Results

Beyond their production of IL-17A, microbiota-induced γδ T cells might promote lung tumorigenesis through other effector mechanisms. To further understand the biology of tumor-associated γδ T cells in the lung and the molecular mechanism(s) by which they mediate inflammation and lung tumor development, their transcriptional profiles in comparison to splenic γδ T cells were characterized using RNA-seq. Results demonstrated that γδ T cells in the tumor-bearing KP lungs exhibited a distinct gene expression signature as compared to their splenic counterparts. The prognostic value of this signature was explored in a human lung adenocarcinoma patient cohort from The Cancer Genome Atlas (TCGA/LUAD, cancergenome.nih.gov). Using RNA-seq data from TCGA, individual patient samples were scored for their correlation with the KP-lung γδ T cell signature. Importantly, high-scoring patients (top 25%, n=128), whose gene expression profiles most correlated with the KP-lung γδ T cell signature, exhibited significantly poorer survival compared to patients with lower scores (bottom 25%, n=128; p=0.016).

Gene set enrichment analysis (GSEA) further revealed that the γδ T cells in the tumor-bearing lungs exhibited a gene expression pattern similar to activated human γδ T cells. Additionally, as tissue-resident lymphocytes, γδ T cells in KP lungs also shared common gene signatures enriched in tissue-resident αβ T cells. Moreover, the robust upregulation of LPS-responsive genes in these KP-lung associated γδ T cells provided further evidence at the transcriptional level that they underwent microbial stimulation from airway microbiota.

Figure 7A:
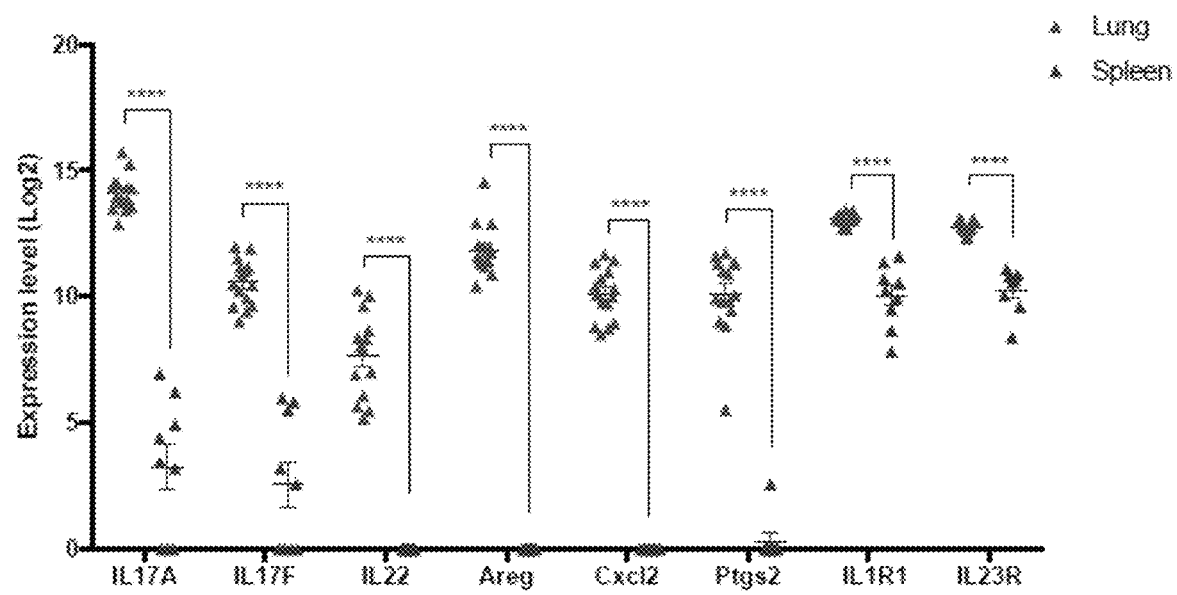
FIG. 7A is a graph showing pairwise comparisons of the RNA-seq expression levels of 8 relevant genes between KP-lung and spleen samples (**** denotes FDR<1.63E-12).

In particular, the transcriptional signature showed a number of genes to be highly upregulated in KP-lung associated γδ T cells in comparison to splenic γδ T cells (FIG. 7A), and these data were further validated at the mRNA and/or protein levels using qPCR and/or flow cytometry. In addition to IL-17A and IL-17F, γδ T cells in the KP lungs also highly expressed other effector molecules that might contribute to tumor-promoting inflammation. For example, CXCL2 is a neutrophil chemoattractant, whereas PTGS2 (prostaglandin-endoperoxide synthase 2) is essential for the biosynthesis of prostaglandin, a potent inflammatory mediator. IL-1R1 and IL-23R expression were also elevated in γδ T cells from tumor-bearing lungs (FIG. 7A), indicative of their enhanced capability of responding to IL-1β and IL-23 induced by microbial products as compared to splenic γδ T cells.

Figure 7B:
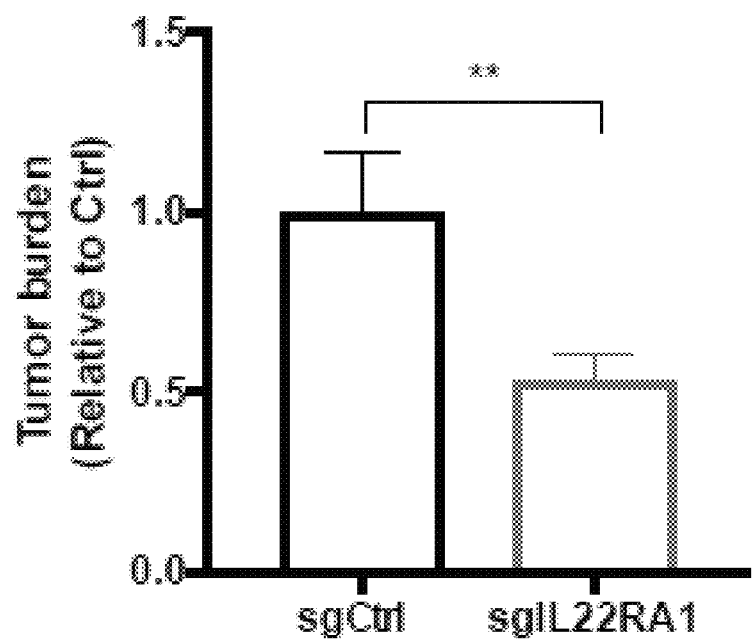
FIG. 7B is a graph showing the tumor burden at 10 weeks post tumor initiation in KP-R26$^{LSL-cas9}$ mice infected with lentiviral vectors co-expressing Cre and sgRNA against IL-22RA1 or an irrelevant locus (sgCtrl).

Furthermore, among the top differentially expressed genes, IL-22 is an epithelial growth factor significantly up-regulated in lung-tumor associated γδ T cells. Although implicated for tumor-promoting effects in colorectal cancer, the role of IL-22 in lung cancer is not well studied. The effects of IL-22 receptor deletion in developing lung cancer cells was tested in the KP model by introducing a lentivirally-encoded sgRNA targeting IL-22RA1 in KP mice harboring the LSL-cas9 allele. Targeting IL-22RA1 led to a significant reduction in tumor burden (FIG. 7B). Moreover, recombinant IL-22 stimulated tumor cell proliferation in vitro. In line with the mouse data, IL-22RA1 expression was found to be substantially elevated in human LUAD samples as compared to healthy lung tissues (p=8.580e-04). When patients were stratified by their levels of IL22RA1 expression, those with high expression (top 30%) exhibited significantly worse survival as compared to the rest of the cohort (p=0.00001), suggesting that elevated IL-22 signaling is correlated with increased mortality rate in LUAD.

Another top-scoring gene in the KP-lung γδ T cell signature was amphiregulin (Areg), which is an epidermal growth factor receptor (EGFR) ligand involved in the homeostasis and repair of epithelial tissue. The results demonstrated a robust expression of amphiregulin in lung tumor-associated γδ T cells at both the mRNA and the protein levels. Furthermore, recombinant amphiregulin promoted proliferation of KP tumor-derived cell lines in a dose-dependent fashion.

These findings, together with the data on the IL-22 pathway, provide strong evidence that microbiota-activated γδ T cells may promote lung cancer progression by directly stimulating tumor cell proliferation, in addition to stimulating inflammation in the lung microenvironment.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of targeting the lung microbiota and its responding immune pathways in a subject having lung cancer, the method comprising, analyzing the bacterial composition in a sample from the subject and then administering to the subject one or more therapeutics in an effective amount to reduce the local bacterial load in the lungs of the subject, block or deplete tumor-infiltrating immune cells in the lungs of the subject, locally inhibit one or more cytokines or chemokines in the lungs of the subject, or a combination thereof,
wherein the one or more therapeutics comprises an antibiotic, wherein the one or more therapeutics does not comprise erythromycin, and
wherein prior to the administration of the therapeutics, the subject does not manifest symptoms of a microbial lung infection.

2. The method of claim 1, wherein the administration of the therapeutics reduces the local bacterial load in the lungs.

3. The method of claim 1, wherein the administration of the therapeutics blocks or depletes tumor-infiltrating immune cells in the lungs.

4. The method of claim 1, wherein the administration of the therapeutics locally inhibits one or more cytokines and/or chemokines or locally inhibits cytokine and/or chemokine activity in the lungs.

5. The method of claim 1, wherein the sample is a sputum sample or bronchoscopy biopsy.

6. The method of claim 1, wherein the analysis comprises microbial culture and 16S-based sequencing.

7. The method of claim 1, wherein the subject is identified as having increased total bacterial load and/or reduced bacterial diversity compared to a healthy subject.

8. The method of claim 1, wherein the subject is identified as having one or more types of bacteria enriched in the lungs of the subject compared to a healthy subject.

9. A method of targeting the lung microbiota and its responding immune pathways in a subject having lung cancer, the method comprising, analyzing the bacterial composition in a sample from the subject and, where the subject is identified as having one or more types of bacteria enriched in the lungs of the subject compared to a healthy subject, administering to the subject one or more therapeutics in an effective amount to reduce the local bacterial load in the lungs of the subject, block or deplete tumor-infiltrating immune cells in the lungs of the subject, locally inhibit one or more cytokines or chemokines in the lungs of the subject, or a combination thereof, wherein the one or more types of bacteria are commensal bacteria selected from Leuconostoceae, Sphingomonadaceae, Alphaproteobacteria, Herbaspirillum, Burkholderiales, or combinations thereof.

10. The method of claim 8, wherein one or more of the therapeutics selectively targets, inhibits, kills, or a combination thereof, one or more of the types of the bacteria enriched in the lungs of the subject.

11. The method of claim 8, wherein one or more of the therapeutics is selected for administration because it can selectively target, inhibit, kill, or a combination thereof, one or more of the types of the bacteria enriched in the lungs of the subject.

12. The method of claim 3, wherein the immune cells are γδ T cells, neutrophils, or a combination thereof.

13. The method of claim 12, wherein the γδ T cells, neutrophils, or both were activated and/or proliferated by stimulation by lung microbiota of the subject.

14. The method of claim 12, wherein the γδ T cells are positive for promyelocytic leukemia zinc finger (PLZF), CD27, CD44, CD69, and/or PD1.

15. The method of claim 4, wherein the one or more cytokines and/or chemokines comprise one or more of IL-1β, IL-23, IL-17, IL-22, amphiregulin, CXCL2, PTGS2, IL-1R1, IL-23R, G-CSF, and IL-22R.

16. The method of claim 1, wherein the one or more therapeutics further comprise one or more antibodies, small molecules, kinase inhibitors, siRNAs, miRNAs, aptamers, natural or engineered autologous or allogenic immune cells, or combinations thereof.

17. The method of claim 1, wherein the antibiotic is a restricted spectrum antibiotic.

18. The method of claim 1, wherein the antibiotic is in an inhalable and/or aerosolized form or formulation.

19. The method of claim 1, wherein the antibiotic is ampicillin, neomycin, metronidazole, vancomycin, azithromycin, clarithromycin, or clindamycin.

20. The method of claim 1, wherein the one or more therapeutics further comprises an antibody.

21. The method of claim 20, wherein the antibody is canakinumab, secukinumab, ixekizumab, brodalumab, risankizumab, guselkumab, or tildrakizumab.

22. The method of claim 1, wherein the lung cancer is lung adenocarcinoma.

23. The method of claim 1, wherein the administration of the therapeutics is by local administration.

24. The method of claim 1, wherein the one or more therapeutics further comprises one or more other targeted therapies and/or immune-checkpoint blockage agents.

25. The method of claim 1, wherein the administration of the therapeutics reduces cancer cell proliferation or viability and/or reduces tumor burden in the subject.

26. The method of claim 1, wherein the reduction in the local bacterial load, block or depletion of tumor-infiltrating immune cells, local inhibition of one or more cytokines or chemokines, or a combination thereof, reduces cancer cell proliferation or viability and/or reduces tumor burden in the subject.

27. A method of targeting the lung microbiota and its responding immune pathways in a subject having lung cancer, the method comprising, administering to the subject one or more therapeutics in an effective amount to reduce the local bacterial load in the lungs of the subject, block or deplete tumor-infiltrating immune cells in the lungs of the subject, locally inhibit one or more cytokines or chemokines in the lungs of the subject, or a combination thereof, wherein the one or more therapeutics is administered by intranasal administration or oral inhalation, wherein prior to the administration of the therapeutics, the subject does not manifest symptoms of a microbial lung infection.

28. A method of targeting the lung microbiota and its responding immune pathways in a subject having lung cancer, the method comprising, administering to the subject one or more therapeutics in an effective amount to reduce the local bacterial load in the lungs of the subject, block or deplete tumor-infiltrating immune cells in the lungs of the subject, locally inhibit one or more cytokines or chemokines in the lungs of the subject, or a combination thereof, wherein the one or more therapeutics comprises an antibiotic, wherein the one or more therapeutics does not comprise erythromycin, and wherein prior to the administration of the therapeutics, the subject does not manifest symptoms of a microbial lung infection.

\* \* \* \* \*